US012600995B2

(12) United States Patent
Bornhövd et al.

(10) Patent No.:  US 12,600,995 B2
(45) Date of Patent:  Apr. 14, 2026

(54) BIOCATALYST AS A CORE COMPONENT OF AN ENZYME-CATALYZED REDOX SYSTEM FOR THE BIOCATALYTIC REDUCTION OF CYSTINE

(71) Applicant: Wacker Chemie AG, Munich (DE)

(72) Inventors: Carsten Bornhövd, Munich (DE); Guido Jach, Königswinter (DE); Ingrid Torres Monroy, Düsseldorf (DE); Peter Welters, Nettetal (DE)

(73) Assignee: WACKER CHEMIE AG, Munich (DE)

( * ) Notice: Subject to any disclaimer, the term of this patent is extended or adjusted under 35 U.S.C. 154(b) by 541 days.

(21) Appl. No.: 17/915,538

(22) PCT Filed: Apr. 3, 2020

(86) PCT No.: PCT/EP2020/059654
§ 371 (c)(1),
(2) Date: Sep. 29, 2022

(87) PCT Pub. No.: WO2021/197632
PCT Pub. Date: Oct. 7, 2021

(65) Prior Publication Data
US 2023/0124898 A1     Apr. 20, 2023

(51) Int. Cl.
*C12P 13/12*      (2006.01)
*C12N 9/02*       (2006.01)
*C12N 15/62*      (2006.01)

(52) U.S. Cl.
CPC ........... *C12P 13/12* (2013.01); *C12N 9/0051* (2013.01); *C12Y 108/01009* (2013.01); *C12Y 108/0401* (2013.01)

(58) Field of Classification Search
CPC ....... C12P 13/12; C12N 9/0051; C12N 15/62; C12Y 108/01009; C12Y 108/0401; C12Y 108/04008; C07K 2319/00
See application file for complete search history.

(56) References Cited

U.S. PATENT DOCUMENTS

| | | | |
|---|---|---|---|
| 5,972,663 A | 10/1999 | Winterhalter et al. | |
| 6,218,168 B1 | 4/2001 | Leinfelder et al. | |
| 2004/0038352 A1 | 2/2004 | Maier | |
| 2019/0055586 A1 | 2/2019 | Fremy et al. | |

FOREIGN PATENT DOCUMENTS

| | | |
|---|---|---|
| CA | 2386539 C | 4/2007 |
| CN | 101899460 B | 6/2013 |
| EP | 2138585 B1 | 2/2011 |
| EP | 1832658 B1 | 7/2011 |
| EP | 1769080 B1 | 9/2013 |
| EP | 2726625 B1 | 7/2015 |
| WO | 2013000864 A1 | 1/2013 |

OTHER PUBLICATIONS

Luthman M. et al., "Rat Liver Thioredoxin and Thioredoxin Reductase: Purification and Characterization", Biochemistry, 1982, vol. 21, pp. 6628-6633. (Year: 1982).*

Wieles B. et al., "Unique gene organization of thioredoxin and thioredoxin reductase in *Mycobacterium leprae*", Molecular Microbiology, 1995, vol. 16, No. 5, pp. 921-929. (Year: 1995).*

B. Wieles et al., Purification and Functional Analysis of the *Mycobacterium leprae* Thioredoxin/Thioredoxin Reductase Hybrid Protein, Journal of Biological Chemistry, 1995, vol. 270, No. 43, p. 25604-25606, The American Society for Biochemistry and Molecular Biology, Inc. (US).

S.H. Lee et al., Cysteine Produced from Lymph Node Stromal Cells Suppresses Apoptosis of Mouse Malignant T-Lymphoma Cells, Biochemical and Biophysical Research Communications, vol. 213, No. 3, 1995, p. 837-844, Academic Press, Inc. (US).

G. H. Coombs, The Amitochondriate Eukaryote Trichonomas vaginalis Contains a Divergent Thioredoxin-linked Peroxiredoxin Antioxidant System, The Journal of Biological Chemistry, vol. 219, No. 7, 2003, pp. 5249-5256, The American Society fur Biochemistry and Molecular Biology, Inc. (US).

\* cited by examiner

*Primary Examiner* — Satyendra K Singh
(74) *Attorney, Agent, or Firm* — BROOKS KUSHMAN P.C.

(57)        ABSTRACT
An enzyme for reducing cystine to cysteine is a fusion protein that includes the protein activities of thioredoxin (protein i) having KEGG database number EC 1.8.4.8 or EC 1.8.4.10 and thioredoxin reductase (protein ii) having KEGG database number EC 1.8.1.9. The thioredoxin (protein i) is the protein activity of thioredoxin 1 from *E. coli* and the thioredoxin reductase (protein ii) is the protein activity of the thioredoxin reductase from *E. coli*. The activity of the fusion protein is at least 100% of the activity of a mixture of the same but unfused individual proteins i and ii. The fusion protein has the enzyme activity to reduce cystine to cysteine. The coding sequences (cds) responsible for the activity of protein i and ii has been fused.

7 Claims, 4 Drawing Sheets

Specification includes a Sequence Listing.

BIOCATALYST AS A CORE COMPONENT OF AN ENZYME-CATALYZED REDOX SYSTEM FOR THE BIOCATALYTIC REDUCTION OF CYSTINE

CROSS-REFERENCE TO RELATED APPLICATION

This application is a U.S. National Phase Application of PCT/EP2020/059654, filed Apr. 3, 2020, the contents of which is hereby incorporated by reference in its entirety.

SEQUENCE LISTING

The text file CO11913 sequence listing ST25 EN, created Aug. 24, 2022, of file size 36 KB, and filed herewith is hereby incorporated by reference.

BACKGROUND

The invention relates to an enzyme for reducing cystine to cysteine, characterized in that the enzyme is a fusion protein that comprises the protein activities of thioredoxin (protein i) having KEGG database number EC 1.8.4.8 or EC 1.8.4.10 and thioredoxin reductase (protein ii) having KEGG database number EC 1.8.1.9, wherein the activity of the fusion protein is at least 100% of the activity of a mixture of the same but unfused individual proteins i and ii. The invention further relates to a process for enzymatically reducing cystine to cysteine in the presence of a cofactor using said fusion protein.

Cysteine, abbreviated Cys or C, is an α-amino acid having the side chain —$CH_2$—SH. Since the naturally occurring enantiomeric form is L-cysteine and since only this is a proteinogenic amino acid, it is in the context of the present invention L-cysteine that is meant when the term cysteine is used without a descriptor. Oxidation of the sulfhydryl groups can result in two cysteine residues together forming a disulfide bond, with consequent formation of cystine, to which the same statement applies, i.e. in the absence of a descriptor it is the L-enantiomer (or R,R-cystine) that is meant in the present invention. L-cysteine is a semi-essential amino acid for humans, since it can be formed from the amino acid methionine.

The amino acid L-cysteine is used for example as a food additive (particularly in the baking industry), as a raw material in cosmetics, and as a starting material for the production of active pharmaceutical ingredients (particularly N-acetylcysteine and S-carboxymethylcysteine) and is accordingly of economic importance. The use of cysteine as a flavoring substance in the food industry (for example as a chicken or meat flavoring) is viewed as particularly important. L-Cysteine is also used to modify the rheology of doughs and as an antioxidant, for example in juices.

In all organisms, L-cysteine plays a key role in sulfur metabolism. It is used for the synthesis of proteins, methionine, biotin, lipoic acid, glutathione, and other sulfur-containing metabolites. L-Cysteine is also used in the biosynthesis of coenzyme A. In enzymes, the thiol group often plays an important role in the catalysis of reactions or stabilizes proteins through the formation of intra- or intermolecular disulfide bonds.

L-Cysteine can be obtained by hydrolysis from keratin-containing materials such as hair, bristles, nails, hooves, feathers, and horns. However, such processes always raise questions about biosafety and environmental protection. They also have low productivity. As an alternative, processes for production by biotransformation from precursors and for the fermentative production of L-cysteine have been developed (U.S. Pat. No. 6,218,168 B1, U.S. Pat. No. 5,972,663 A, US 2004-038352 A, CA 2 386 539 A2, EP 2 138 585, EP 1 769 080, and EP 2 726 625 B1).

A disadvantage of the fermentative production is a low yield of L-cysteine (even after optimized fermentation control), which is also because cysteine oxidizes in the presence of atmospheric oxygen and is then present mainly as the disulfide L-cystine and can be obtained in this form.

The oxidation reaction is reversible, consequently the L-cystine can be converted back into L-cysteine by selective reduction. However, if L-cystine is reduced back to L-cysteine by electrolysis after separation from the cells (for example using a decanter), this chemical conversion means that such L-cysteine may not be declared as natural according to the Regulation on Flavorings.

According to the EU Regulation on Flavorings (1334/2008 Article 22 of the regulation on the reorganization of food labeling regulations), natural flavors are defined as follows: "Natural" flavorings are chemically defined substances with flavoring properties that occur naturally and have been detected in nature. They are obtained by suitable physical, enzymatic or microbiological processes from starting materials of plant, animal or microbiological origin, which are used as is or are prepared for human consumption by means of one or more conventional food preparation processes.

The term "natural" is used in this sense too in the present application. There is great interest in the use of natural raw materials in the production of flavorings.

An enzymatic cleavage would permit the production of a natural cysteine, with use made of the high fermentative cystine yields. For the performance of such an enzymatic process, a suitable redox enzyme cascade system is required. Examples of disulfide-cleaving enzymes that have been described include thioredoxins, glutaredoxins, and disulfide isomerases. However, these enzymes most often act on disulfides that have formed within a polypeptide or between two subunits of a protein. The cleavage of free cystine has been described only for a few proteins, for example for bacterial thioredoxin, which in turn is regenerated by thioredoxin reductase, for which NADPH is needed as a cofactor. Such redox enzymes or enzyme cascades often require NADH or NADPH as a cofactor that provides the corresponding electrons for the reduction reaction.

A cystine reductase is accordingly characterized in that it uses the substrate cystine and, with the aid of a cofactor such as NADPH or NADH, transfers two electrons, with the formation of two cysteines as the end product.

This means that the cofactor must therefore be added to the reaction in equimolar amounts, which is cost-intensive and therefore economically unfavorable. This can be avoided by coupling with a second reaction to regenerate the cofactor. As a regenerative system, it is possible to use dehydrogenases such as alcohol dehydrogenase or glucose-6-phosphate dehydrogenase. From an economic point of view, it must be possible to produce these enzymes too by fermentation with a correspondingly high yield.

Since the effort involved in producing the required enzymes increases with the number of enzymes, it makes economic sense to fuse the individual enzymes by genetic engineering. This can have the additional advantage that the substrates are able to migrate more easily from one enzyme to the next by virtue of the close spatial proximity. However, such enzyme fusions often result in poorer fermentative producibility or else the fusion protein has reduced activity or even no activity at all. In order to prevent the two enzymes from having a mutually inhibitory effect in the fusion protein, longer linker sequences that connect/separate the two proteins are instead often employed. It is rare for fusion proteins to show comparable activities compared to mixtures of the starting proteins, when very short linker sequences or no linker sequences at all are employed.

In *Mycobacterium leprae* (Wieles B. et al. 1995, J. Biol. Chem. 270, pp. 25604-25606), a protein is found that is active as thioredoxin and thioredoxin reductase, the N-terminus of the protein being homologous to thioredoxin reductase and the C-terminus homologous to thioredoxin. On comparing the two protein units with the homologous proteins from *E. coli*, these are in *M. leprae* connected via a 22-amino acid spacer/linker.

The object of the present invention is to provide a protein for the biocatalytic reduction of cystine to cysteine that can be produced inexpensively and that has an activity at least as high as a mixture of the thioredoxin and thioredoxin reductase proteins known in the prior art. By using this protein in a process for enzymatically reducing cystine to cysteine, a particularly efficient and economical process should be provided.

BRIEF SUMMARY

Embodiments of an enzyme for reducing cystine to cysteine are provided. In an embodiment, the enzyme is a fusion protein that comprises the protein activities of thioredoxin (protein i) having KEGG database number EC 1.8.4.8 or EC 1.8.4.10 and thioredoxin reductase (protein ii) having KEGG database number EC 1.8.1.9. The thioredoxin (protein i) is the protein activity of thioredoxin 1 from *E. coli* and the thioredoxin reductase (protein ii) is the protein activity of the thioredoxin reductase from *E. coli*. The activity of the fusion protein is at least 100% of the activity of a mixture of the same but unfused individual proteins i and ii. The fusion protein has the enzyme activity to reduce cystine to cysteine. The coding sequences (cds) responsible for the activity of protein i and ii has been fused.

BRIEF DESCRIPTION OF THE SEVERAL VIEWS OF THE DRAWING

The above, as well as other advantages of the present invention will become readily apparent to those skilled in the art from the following detailed description when considered in the light of the accompanying drawings in which.

Figure 1:
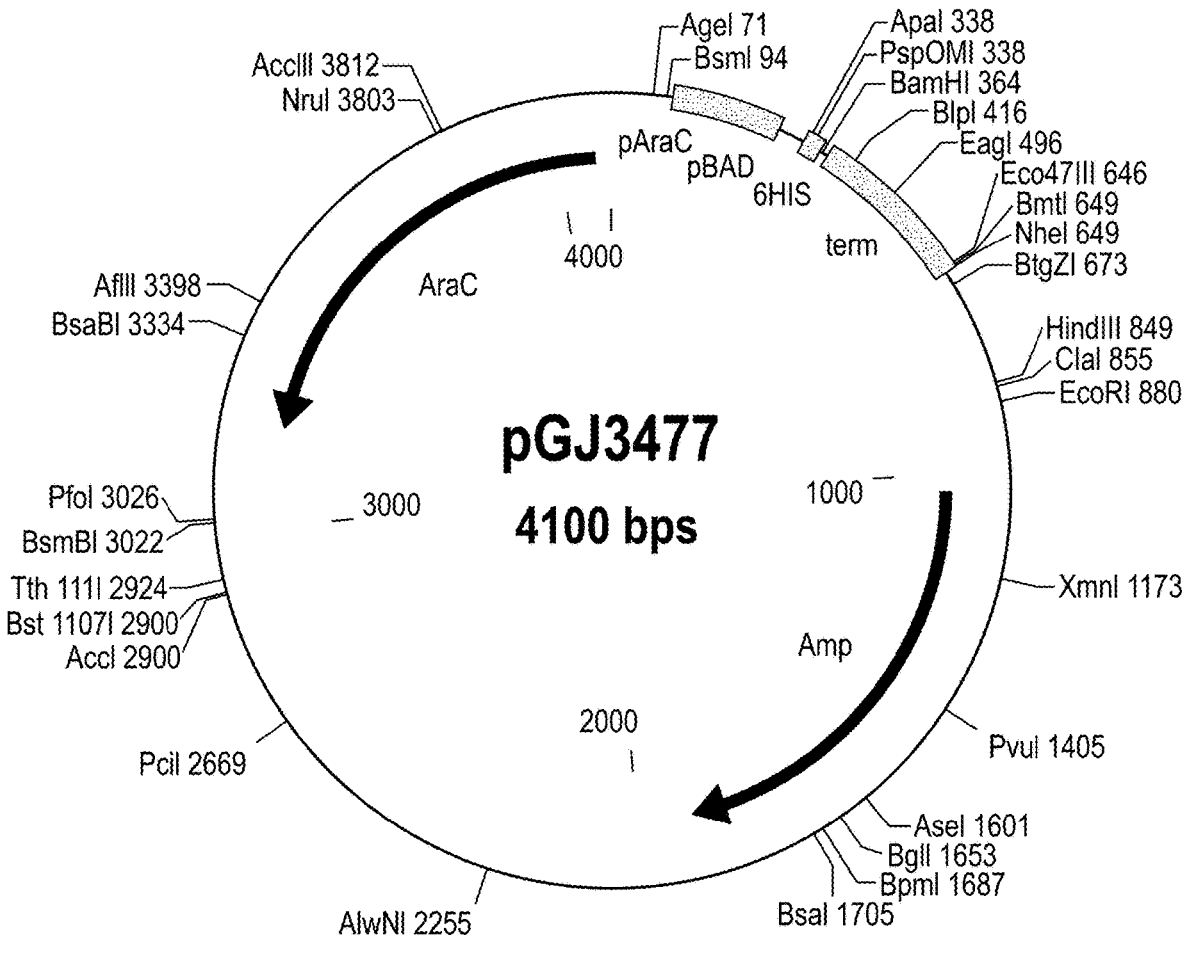
FIG. 1 shows the plasmid map of the plasmid pGJ3477.

This object is achieved by providing an enzyme for reducing cystine to cysteine, characterized in that the enzyme is a fusion protein that comprises the protein activities of thioredoxin (protein i) having KEGG database number EC 1.8.4.8 or EC 1.8.4.10 and thioredoxin reductase (protein ii) having KEGG database number EC 1.8.1.9, wherein the activity of the fusion protein is at least 100% of the activity of a mixture of the same but unfused individual proteins thioredoxin and thioredoxin reductase.

According to the invention, the enzyme for reducing cystine to cysteine is a fusion protein that includes the protein activities of proteins i and ii. This means that the coding sequences (cds) responsible for the activity of protein i (Trx, described in KEGG database number EC 1.8.4.8 or EC 1.8.4.10) and the activity of protein ii (TR, described in KEGG database number EC 1.8.1.9) are fused. By removing the stop codon present after the first cds, the two cds are expressed together as a single cds. The protein activity of Trx is an oxidoreductase that has a disulfide bond in the active site and can exist in a reduced or oxidized state.

In the reaction, two electrons are transferred from the two sulfhydryl groups to a disulfide bond (intra- or intermolecularly). An intramolecular disulfide bond is here formed in Trx. The reduced state of the Trx is then restored by the catalytic activity of the oxidoreductase TR. This requires electrons, which are transferred to Trx with cleavage of the disulfide bond.

Whether a protein is active as Trx and/or TR toward cystine (hereinafter referred to as cystine reductase/CR activity when the protein has both activities) can be checked with the aid of the following test:

Firstly, the consumption of NADPH can be measured photometrically at 340 nm. In a mixture comprising the fusion protein, the substrate cystine, and the cofactor NADPH, electrons are transferred from NADPH to the cystine, with the formation of cysteine. The consumption of NADPH can then be monitored photometrically.

Alternatively, the cysteine that is formed can also be measured in such a mixture (comprising fusion protein, cystine, and NADPH). This makes use of the ability of the free —SH group of the cysteine to react with DTNB (5,5'-dithiobis-2-nitrobenzoic acid; Ellman's reagent) with the formation of a dye. This colored compound Cys-TNB can be measured at 412 nm. The course of this reaction over time thus allows the enzyme activity of the fusion protein toward cystine to be measured.

Protein i and protein ii are preferably microbial sequences.

The thioredoxin (protein i) is preferably the protein activity of thioredoxin 1 from *E. coli* (abbreviated to TrxA in the context of the present invention).

The thioredoxin reductase (protein ii) is preferably the protein activity of the thioredoxin reductase from *E. coli* (abbreviated to TrxB in the context of the present invention).

It is particularly preferable that the fusion protein comprises two amino acid sequences, wherein one of these amino acid sequences is at least 50%, preferably at least 70%, and particularly preferably at least 90%, identical to SEQ ID No. 7 and the other amino acid sequence is at least 50%, preferably at least 70%, and particularly preferably at least 90%, identical to SEQ ID No. 8, and wherein the fusion protein has CR activity.

The fusion protein is accordingly designated TrxAB or TrxBA/TrxB5A, wherein in fusion protein TrxAB the protein TrxA is located N-terminally to TrxB. Conversely, in fusion protein TrxBA or TrxB5A, the protein TrxB is located N-terminally to TrxA. It is preferable that the fusion protein is TrxAB, TrxBA or TrxB5A. The fusion protein is particularly preferably a fusion of the amino acid sequences of thioredoxin A and thioredoxin B from *E. coli*, especially preferably one of the amino acid sequences selected from the group consisting of SEQ ID No. 9, SEQ ID No. 10, and SEQ ID No. 28.

In a particularly preferred embodiment, the fusion protein is TrxBA, especially preferably the amino acid sequence having SEQ ID No. 10.

The degree of DNA identity is determined by the "nucleotide blast" program, which can be found at blast.ncbi.nlm-.nih.gov and is based on the blastn algorithm. The default parameters were used as the algorithm parameters for an alignment of two or more nucleotide sequences. The default general parameters are: Max target sequences=100; Short queries="Automatically adjust parameters for short input sequences"; Expect Threshold=10; Word size=28; Automatically adjust parameters for short input sequences=0. The corresponding default scoring parameters are: Match/Mismatch Scores=1,–2; Gap Costs=Linear.

Protein sequences are compared using the "protein blast" program at blast.ncbi.nlm.nih.gov. This program uses the blastp algorithm. The default parameters were used as the algorithm parameters for an alignment of two or more protein sequences. The default general parameters are: Max target sequences=100; Short queries="Automatically adjust parameters for short input sequences"; Expect Threshold=10; Word size=3; Automatically adjust parameters for short input sequences=0. The default scoring parameters are: Matrix=BLOSUM62; Gap Costs=Existence: 11 Extension: 1; Compositional adjustments=Conditional compositional score matrix adjustment.

In the context of the present invention, the proteins such as TrxA, TrxB, TrxAB, TrxBA, TrxB5A or MI-TrxBA start with a capital letter, whereas the sequences coding for these proteins (also abbreviated to cds) are identified with a lower case letter (trxA, trxB, trxAB, trxBA, trxB5A or MI-trxBA).

In the context of the invention, the term fusion protein means that the protein comprises the two individual proteins thioredoxin (Trx) and thioredoxin reductase (TR). It is encoded by a gene, the coding region of which comprises the Trx coding region and the TR coding region, with the result that they are together as a single unit transcribed and translated into a polypeptide.

A particular advantage of using a fusion protein containing Trx and TR, compared to using the two individual proteins Trx and TR, arises from the position in space of the two proteins: TR transfers electrons to Trx, wherein Trx and TR do not first need to encounter one another in a three-dimensional diffusion process, but are connected to one other in the fusion protein. In other words, the spatial proximity means that the electrons can pass from one enzyme to the other more easily.

Whereas the individual proteins must be purified separately, the enzyme activities in the fusion protein are isolated together, which is also a great economic advantage.

Preferably, the fusion protein additionally includes a sequence as an aid to purification such as, particularly preferably, a polyhistidine tag (His-tag). A His-tag is a protein tag that can be used for protein purification and for the detection of tagged proteins. The amino acid sequence of the polyhistidine tag is a sequence of at least six histidines (6HIS), the gene sequence of which is cloned into the cds N-terminally after the start methionine codon or C-terminally before the stop codon. This creates a fusion protein having a polyhistidine tag. Cloning of just one His-tag makes it possible to purify a fusion protein composed of the proteins Trx and TR. Not only does this mean that fewer reaction steps are necessary for purification, but the cloning strategy too is simplified.

In addition, it is possible to insert a cleavage site for a protease or an intein between the polypeptide sequence and the His-tag, so as to make it possible for the His-tag to be cleaved off after protein purification.

It is preferable that the amino acid sequence of the protein located N-terminally is in the fusion protein shortened C-terminally by one to at most five amino acids. It is particularly preferable that the amino acid sequence of the protein located N-terminally is in the fusion protein shortened C-terminally by one amino acid.

It is preferable that the amino acid sequence of the protein located C-terminally is in the fusion protein shortened N-terminally by one to at most five amino acids, particularly preferably by one amino acid. Particularly preferably, the start codon is absent in the protein located C-terminally in the fusion protein. This latter feature has the advantage that there is no risk of translation beginning afresh at this point.

In addition, it is preferable that the amino acid sequences of the fused protein activities of thioredoxin (protein i) and thioredoxin reductase (protein ii) are in the fusion protein connected by a linker sequence of one to at most five amino acids, particularly preferably of one amino acid.

It is particularly preferable that the amino acid sequences of the fused proteins thioredoxin (protein i) and thioredoxin reductase (protein ii) follow one another directly in the fusion protein, i.e. there is no linker sequence present.

As stated above, it is advantageous to bring together, in a fusion protein, proteins that act in concert so as to improve their cloning, purification, and activity. However, in order not to hinder the folding of the two fusion proteins or the interaction therebetween that is necessary in this case, the use of a long linker sequence would seem advisable. However, it was surprisingly found that in this case direct fusion of the two proteins (Trx, TR) resulted in a functional enzyme pair. This is underscored by the finding that the activity of the fusion protein depends on the order of fusion. Thus, the fusion protein TrxAB exhibited an activity comparable to a mixture of the individual proteins.

In the fusion protein TrxAB (SEQ ID No. 9), the stop codon is absent in the TrxA sequence (SEQ ID No. 7), while in TrxB (SEQ ID No. 8) the first amino acid (methionine, M) has been deleted. In addition, the protein carries a His-tag (amino acids 1-12 in SEQ ID No. 9). No linker sequence is present between the last amino acid of TrxA (Ala) and the first amino acid of TrxB (Gly) after removal of the start codon.

In the fusion protein TrxBA (SEQ ID No. 10), the last amino acid (lysine) and the stop codon are absent in the TrxB sequence (SEQ ID No. 8), while in TrxA (SEQ ID No. 7) the first amino acid (methionine, M) has been deleted. In addition, the protein carries a His-tag (amino acids 1-12 in SEQ ID No. 10). A linker sequence of one amino acid (Gly) is present between the penultimate amino acid of TrxB (Ala) and the first amino acid of TrxA (Ser).

For the fusion protein TrxB5A (SEQ ID No. 28), the same applies as described for TrxBA, with the exception that there is a linker sequence of five amino acids (Gly-Pro-Ala-Pro-Gly) between TrxB and TrxA.

The region located between a start codon and a stop codon that codes for the amino acid sequence of the fusion protein is referred to as the coding sequence (cds). Cds are surrounded by non-coding regions. What is referred to as a gene is the section of DNA that contains all the basic information for producing a biologically functional protein. A gene contains the section of DNA from which a single-stranded RNA copy is produced by transcription and also the expression signals involved in the regulation of this copying process. The expression signals include for example at least one promoter, a transcription start, a translation start, and a ribosome binding site. In addition, expression regulation by a terminator and one or more operators is possible. For a functional promoter, the cds under the regulation of this promoter is transcribed into an RNA.

The section of DNA encoding protein i of the fusion protein (thioredoxin) can first be amplified by PCR using oligonucleotides as primers and a DNA matrix encoding thioredoxin, for example genomic DNA isolated from *E. coli*, and then coupled by means of standard molecular biological techniques with in each case the DNA molecule that includes the protein ii sequence of the fusion protein (thioredoxin reductase) and that was generated in analogous manner, in such a way that an in-frame fusion occurs. The second start codon of the C-terminally located fusion partner that is present in the fusion protein between proteins i and ii can be deleted in order to avoid an alternative reading frame. At the transition point of the two fusion partners, linker sequences of varying length can be inserted.

As an alternative to fusion via cloning sites, the entire DNA molecule can be produced by gene synthesis. This DNA molecule can then either be introduced into a vector, for example a plasmid, or integrated directly into the chromosome of the bacterial strain by known methods. Preferably the DNA molecule is introduced into a plasmid, for instance a derivative of known expression vectors such as pJF118EH, pKK223-3, pUC18, pBR322, pACYC184, pASK-IBA3, pGJ3477 or pET.

It is preferable that the DNA molecule primarily carries the coding sequence of the fusion protein and few other nucleotides and so is cloned into the plasmid such that cloning takes place at a defined distance from the promoter and terminator, i.e. the DNA molecule is cloned into the plasmid at the 3' of a region encoding the promoter and at the 5' of a region encoding the terminator.

Suitable promoters are all promoters known to those skilled in the art, such as constitutive promoters, for example the GAPDH promoter, or inducible promoters, for example the lac, tac, trc, lambda PL, araB, cumate or tet promoter or sequences derived therefrom. The fusion protein is particularly preferably expressed under the control of the arabinose-inducible araB promoter ($P_{BAD}$).

The plasmids used can carry selection markers. Suitable as selection markers are genes coding for resistance to antibiotics such as ampicillin, tetracycline, chloramphenicol, kanamycin or others. The plasmid preferably contains a gene the expression of which confers ampicillin resistance. Also suitable as selection markers are auxotrophy markers, since they code for an essential gene in metabolism that is deleted in the respective bacterial strain that contains the plasmid.

Plasmids can be introduced into the cells of a bacterial strain (transformation) using methods known to those skilled in the art. The bacterial strain is preferably characterized in that the bacterial strain is a Gram-negative bacterium, particularly preferably a bacterial strain of the genus Enterobacteriaceae, especially preferably a strain of the species *Escherichia coli* (*E. coli*).

The bacterial strain containing the plasmid may be used in a fermentation process, i.e. the bacterial cells may be propagated in medium, preferably in selective LB medium (corresponding to the selection marker present in the plasmid), and are after culturing separated from the medium by sedimentation with discarding of the supernatant, and lysed.

The expressed fusion protein can then be isolated, for example by affinity chromatography (for example via a His-tag, see above).

The enzyme of the invention has the advantage that it can be produced by fermentation in high yield and therefore inexpensively. Its production is particularly economically effective and advantageous also because only one fusion protein needs to be produced, purified, and isolated instead of two separate proteins.

It is advantageous that the enzyme can be regenerated by a cofactor such as NADPH or NADH as an electron donor and thus as a reducing agent, since systems for regenerating NADPH or NADH already exist.

The enzyme activities of Trx and TR can be determined via the conversion of the cofactor, for example photometrically at 340 nm. This is possible because the extinction coefficient at 340 nm changes significantly when going from the reduced (NADPH/NADH) to the oxidized (NADP/NAD) state.

On measuring the enzyme activities of various constructs (fusion proteins) or of various mixing ratios of the individual proteins it was a surprise, and for those skilled in the art unforeseeable, to find that the activity of the fusion protein is at least 100%, preferably at least 150%, and particularly preferably at least 200%, of the activity of a mixture of the same but unfused individual proteins thioredoxin and thioredoxin reductase. This means that the activity of the fusion protein is just as high or even higher than that of a mixture of the same but unfused single proteins i and ii.

More precisely, this means that, except in the case of the negative controls without cofactor or substrate, the same reaction mixture consisting of substrate, cofactor, and buffer system was in each case initially charged. After adding the same amount of fusion protein to a mixture, or of the individual proteins i (Trx) and ii (TR) to another mixture, the cofactor conversion was determined in the same time under the same reaction conditions. Alternatively, it is equally possible to detect the decrease in the amount of substrate or the increase in the amount of product.

The enzyme is preferably characterized in that the gene of the fusion protein includes one DNA sequence that is at least 50%, preferably at least 70%, and particularly preferably at least 90%, identical to SEQ ID No. 2 and another that is at least 50%, preferably at least 70%, and particularly preferably at least 90%, identical to SEQ ID No. 3.

In a particularly preferred embodiment, the DNA sequence encoding the fusion protein is SEQ ID No. 5.

The invention further provides a process for enzymatically reducing cystine to cysteine, characterized in that cysteine is reduced by the enzyme of the invention in the presence of a cofactor.

In the enzymatic reduction of cystine to cysteine, a disulfide (—S—S—) is converted into two sulfhydryl (—SH) groups, i.e. two molecules of L-cysteine are formed from one molecule of the chemical compound cystine. The fusion protein of the invention catalyzes the reduction and transfers electrons to the disulfide of the cystine.

Figure 4:
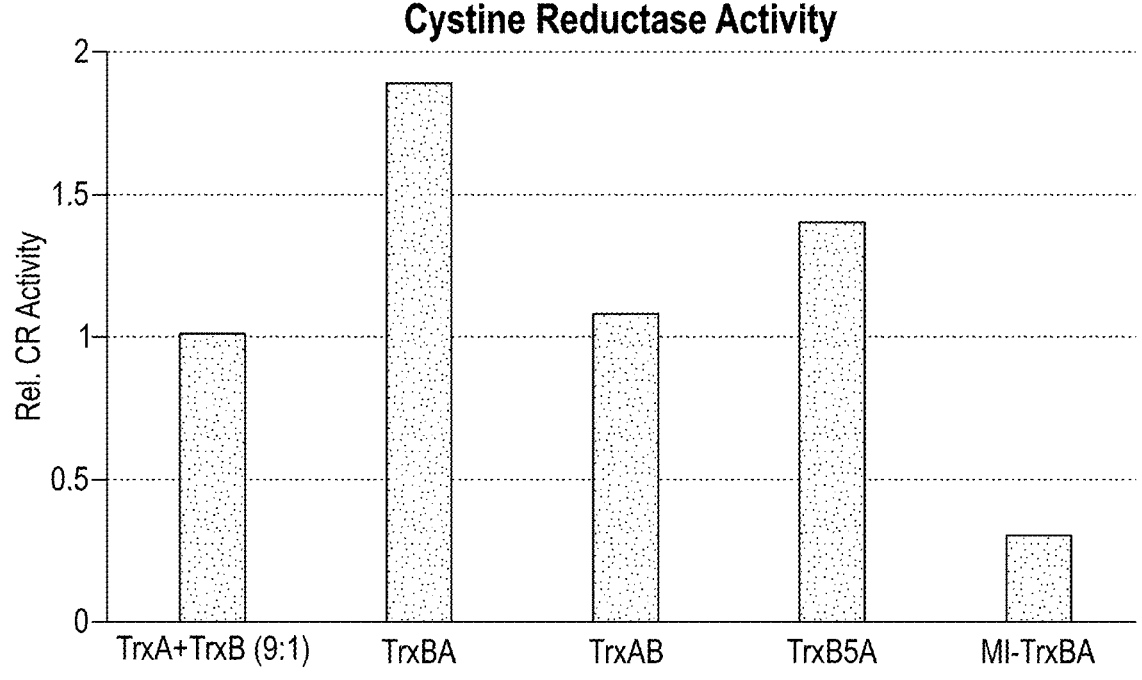
FIG. 4 is a graph illustrating the relative cystine reductase activity of various enzymes.

A surprise here was that the activity of the fusion protein TrxBA was in particular markedly higher than the activity of a mixture of the same but unfused individual proteins TrxA and TrxB (see example 4, FIG. 4).

A particular advantage of the process of the invention is that the cysteine produced using the process can be declared as natural cysteine in accordance with the Regulation on Flavorings.

A further challenge for an economical process was the poor solubility of cystine in buffer systems in a neutral pH range (or in a physiological pH range, i.e. at a pH of approx. 7.4).

The process preferably takes place within a pH range of from 4 to 11, particularly preferably from 5 to 10, and especially preferably from 6 to 9.

It is a particular advantage and therefore additionally particularly preferable when the enzyme of the invention is used in a process for enzymatically reducing cystine to cysteine at physiological pH.

The process preferably takes place at a temperature of 20 to 40° C., particularly preferably from 25 to 30° C.

The process is preferably characterized in that the cofactor is a substance selected from the group consisting of NADPH and NADH. The cofactor is particularly preferably NADPH.

The process is preferably characterized in that, after the reduction, the cysteine formed is isolated. For further purification of the target product, the following steps/procedures can be employed:

isolation of the L-cysteine by ion-exchange adsorption precipitation crystallization.

Such processes are known from the prior art (see for example, WO 2013/000864).

In the reduction of cystine to cysteine, the enzyme of the invention is oxidized, i.e. it transfers electrons to cystine with the formation of a disulfide bond. Since the electrons of the NADPH or NADH cofactor present are transferred to the fusion protein (Trx portion) by the activity of the fusion protein (TR portion), $NADP^+$ or $NAD^+$ respectively are formed. For this reason it is preferable that the process includes a cofactor-regenerating enzyme. Particularly preferably, the cofactor-regenerating enzyme is a dehydrogenase, with the reduction additionally taking place in the presence of a further electron donor.

The cofactor-regenerating enzyme may be a glucose-6-phosphate dehydrogenase and/or the alcohol dehydrogenase. In a particularly preferred embodiment, the dehydrogenase is the alcohol dehydrogenase, with isopropanol used as the electron donor.

The invention is described in more detail hereinbelow with reference to exemplary embodiments, without being restricted thereto.

EXAMPLES

Example 1: Generation of the Cystine Reductase System TrxA, TrxB, TrxBA, and TrxAB Preparation of the Expression Vector:

As the vector for the expression of the DNA sequences coding for the corresponding candidate proteins TrxA, TrxB, TrxAB, TrxBA, TrxB5A or MI-TrxBA, the expression plasmid pGJ3477 was selected. This is a medium- to high-copy plasmid (50-60 copies per cell) based on the ColE1 origin of replication. The plasmid map is shown in FIG. 1, in which the positions of common, only single-cutting restriction enzymes (with 6-base recognition sequence) are indicated on the plasmid map. The sequence is specified in SEQ ID No. 11.

In this plasmid, the coding sequence of the respective candidate was placed under the control of the arabinose-inducible promoter $P_{BAD}$.

First, the entire expression plasmid was amplified by inverse PCR:

50 ng of pGJ3477 DNA, 0.5 pmol of the respective primers 3477-fwrd (SEQ ID No. 12) and 3477-rev (SEQ ID No. 13), Q5® reaction buffer (New England Biolabs, NEB), 1 unit of Q5® DNA polymerase (NEB) in an end volume of 50 µl.

PCR program: 1 min at 98° C., then 30 cycles of 30 s at 98° C., 30 s at 65° C. (annealing), and 2 min at 72° C. (synthesis).

At the end of the reaction, the restriction enzyme Dpnl (10 units, NEB) was added to the reaction mix and the mixture was incubated at 37° C. for 1 h. This was followed by chromatographic purification of the DNA (Macherey & Nagel: NucleoSpin® Gel and PCR Clean-up-Kit).

Cloning of trxA and trxB:

For the cloning of the protein-coding sequences trxA (SEQ ID No. 2) and trxB (SEQ ID No. 3), oligonucleotide primers were defined, the target-gene-specific sequences of which were extended by at least 15 nucleotides, which were overlapping with the sequences at the end of the vector DNA. The genes were amplified by PCR from the E. coli genome of BL21 (colony PCR).

The following mixtures were chosen for amplification by PCR:

50 ng of genomic E. coli BL21 DNA (NEB), 0.5 pmol of the respective primers trxA-fwrd (SEQ ID No. 14) and trxA-rev (SEQ ID No. 15) or trxB-fwrd (SEQ ID No. 16) and trxB-rev (SEQ ID No. 17), Q5® reaction buffer (NEB), 1 unit of Q5® DNA polymerase (NEB) in an end volume of 50 µl.

PCR program: 1 min at 98° C., then 30 cycles of 30 s at 98° C., 30 s at 60° C. (annealing), and 15 s (trxA) or 30 s (trxB) at 72° C. (synthesis).

At the end of the reaction, the restriction enzyme Dpnl (10 units, NEB) was added to the reaction mix and the mixture was incubated at 37° C. for 1 h. This was followed by chromatographic purification of the DNA (Macherey & Nagel: NucleoSpin® Gel and PCR Clean-up-Kit).

LIC-PCR:

In general, the protein-coding DNA sequences were introduced base-exactly into the basic expression vector pGJ3477 via LIC-PCR (ligation-independent-cloning of PCR products) as described in Aslanidis C. and de Jong P. J., Nucleic Acids Res. 18, pp. 6069-6074).

For this purpose, 50 ng of the purified coding DNA of the respective candidate protein was used in the LIC-PCR reaction together with 50 ng of the prepared vector DNA. The LIC-PCR mixture was then, using standard methods, transformed in E. coli XL1 Blue cells and plated on selective LB medium (LB+100 mg/L ampicillin) and incubated at 37° C. for 18 h. For identification of correct clones, plasmid DNA was isolated from the colonies obtained and the expression cassette was fully sequenced. The resulting plasmids, which were composed of the expression vector pGJ3477 and the coding DNA sequence trxA or trxB, were referred to hereinafter as the trxA or trxB expression vector.

Cloning of trxAB and trxBA:

The cloning of the DNA trxAB or trxBA respectively encoding the corresponding fusion protein TrxAB or TrxBA was carried out in analogous manner to the cloning of trxA and trxB as described above, by inserting the trxA sequence into the trxB expression vector by LIC-PCR between the N-terminal his-tag and the sequence trxB encoding the protein TrxB or by inserting the trxB sequence into the trxA expression vector by LIC-PCR between the his-tag and the sequence trxA encoding the protein TrxA:

The following mixtures were chosen for amplification by PCR:

The vector DNA (trxA or trxB expression vector) was amplified by inverse PCR with the primers vtrxA-fwrd (SEQ ID No. 18) and 3477-rev (SEQ ID No. 13) or vtrxB-fwrd (SEQ ID No. 21) and 3477-rev (SEQ ID No. 13), for which the following PCR program was selected: 2 min at 98° C., then 30 cycles of 45 s at 98° C./30 s at 60° C./2.5 min at 72° C.

The trxA or trxB gene segments for the fusion proteins were amplified by PCR with the primers ftrxA-fwrd (SEQ ID No. 22) and ftrxA-rev (SEQ ID No. 23) or ftrxB-fwrd (SEQ ID No. 19) and ftrxB-rev (SEQ ID No. 20), for which the following PCR program was selected: 2 min at 98° C.→then 30 cycles of 45 s at 98° C./30 s at 60° C./15 s at 72° C. BL21 genomic DNA was used as a template.

At the end of the PCR reactions, the restriction enzyme Dpnl (10 units, NEB) was added to the respective reaction mix and the mixture was incubated at 37° C. for 1 h.

This was followed by chromatographic purification of the insert DNA (Macherey & Nagel; NucleoSpin® Gel and PCR Clean-up-Kit).

The LIC-PCR reaction was carried out using 50 ng of the amplified vector DNA of the trxA or trxB expression vector and 75 ng of the insert DNA (trxB or trxA).

The LIC-PCR mixture was then, using standard methods, transformed in *E. coli* XL1 Blue cells and plated on selective LB medium (LB+100 mg/L ampicillin) and incubated at 37° C. for 18 h. For identification of correct clones, plasmid DNA was isolated from the colonies obtained and the expression cassette was fully sequenced.

SEQ ID No. 9 and SEQ ID No. 10 specify the amino acid sequences of the fusion proteins TrxBA and TrxAB resulting respectively from the expression of the sequences SEQ ID No. 4 and SEQ ID No. 5.

Example 2: Cloning of Cystine Reductase MI-TrxBA

As described in the introduction, *Mycobacterium leprae* possesses a gene segment that encodes for the protein with homology to thioredoxin (Trx) and thioredoxin reductase (TR) (Wieles B. et al. 1995, J. Biol. Chem. 270, pp. 25604-25606). The sequence can be taken from the public databases (NCBI Reference Sequence: WP_010909042.1).

The sequence taken from the public databases was customized in silico to the codon usage of the host *E. coli*. This was done using the IDT web server (www.idtdna.com). For cloning into the target vector pGJ3477, the coding region was extended at the 5' and 3' ends by sequences that overlap with the vector sequence (see also cloning of trxA and trxB). The resulting total DNA sequence was produced synthetically (specified in SEQ ID No. 24) by Geneart (www.thermofisher.com) and designated MI-trxBA (also referred to as ml-trxBA).

The synthetic MI-trxBA sequence was cloned into the vector pGJ3477 in analogous manner to the cloning of the trxA and trxB expression vectors by LIC-PCR.

For the cloning of the protein-coding sequence MI-trxBA (SEQ ID No. 24), oligonucleotide primers were defined, the target-gene-specific sequences of which were extended by at least 15 nucleotides, which were overlapping with the sequences at the end of the vector DNA. The synthetic gene served as a template.

The following mixtures were chosen for amplification by PCR:

20 ng of the template (Geneart), 0.5 pmol of the respective primers MI-trxBA-fwrd (SEQ ID No. 25) and MI-trxBA-rev (SEQ ID No. 26), Q5® reaction buffer, 1 unit of Q5® DNA polymerase (NEB) in an end volume of 50 μl.

PCR program: 1 min at 98° C., then 30 cycles of 30 s at 98° C., 30 s at 60° C. (annealing), and 60 s at 72° C. (synthesis).

At the end of the reaction, the restriction enzyme Dpnl (10 units, NEB) was added to the reaction mix and the mixture was incubated at 37° C. for 1 h. This was followed by chromatographic purification of the DNA (Macherey & Nagel: NucleoSpin® Gel and PCR Clean-up-Kit).

LIC-PCR:

The protein-coding DNA sequence was introduced base-exactly into the basic expression vector pGJ3477 via LIC-PCR (ligation-independent-cloning of PCR products) as described in Aslanidis C. and de Jong P. J., Nucleic Acids Res. 18, pp. 6069-6074).

For this purpose, 50 ng of the purified coding DNA was used in the LIC-PCR reaction together with 60 ng of the prepared vector DNA.

The LIC-PCR mixture was then, using standard methods, transformed in *E. coli* XL1 Blue cells and plated on selective LB medium (LB+100 mg/L ampicillin) and incubated at 37° C. for 18 h. For identification of correct clones, plasmid DNA was isolated from the colonies obtained and the expression cassette was fully sequenced. The resulting plasmid, which was composed of the expression vector pGJ3477 and the coding DNA sequence MI-trxBA, was referred to hereinafter as the MI-trxBA expression vector.

Example 3: Cloning of Cystine Reductase TrxB5A (with Linker Sequence)

Cloning of trxB5A:

The cloning of the DNA trxB5A encoding the corresponding fusion protein TrxB5A was carried out in analogous manner to the cloning of trxBA as described above, by inserting a TrxB sequence extended C-terminally by 5 amino acids (referred to hereinafter as TrxB5, and the cds as trxB5) into the trxA expression vector by LIC-PCR between the his-tag and the sequence trxA encoding the protein TrxA:

The following mixtures were chosen for amplification by PCR:

The vector DNA (trxA expression vector) was amplified by inverse PCR with the primers vtrxA5-fwrd (SEQ ID No. 29) and 3477-rev (SEQ ID No. 13), for which the following PCR program was selected: 2 min at 98° C., then 30 cycles of 45 s at 98° C./30 s at 60° C./2.5 min at 72° C.

trxB5 was amplified by PCR with the primers ftrxB-fwrd (SEQ ID No. 19) and ftrxB5-rev (SEQ ID No. 30), for which the following PCR program was selected: 2 min at 98° C.→then 30 cycles of 45 s at 98° C./30 s at 60° C./15 s at 72° C. BL21 genomic DNA was used as a template.

At the end of the PCR reactions, the restriction enzyme Dpnl (10 units, NEB) was added to the respective reaction mix and the mixture was incubated at 37° C. for 1 h. This was followed by chromatographic purification of the insert DNA (Macherey & Nagel; NucleoSpin® Gel and PCR Clean-up-Kit).

The LIC-PCR reaction was carried out using 50 ng of the amplified vector DNA of the trxA expression vector and 75 ng of the insert DNA (trxB5).

The LIC-PCR mixture was then, using standard methods, transformed in *E. coli* XL1 Blue cells and plated on selective LB medium (LB+100 mg/L ampicillin) and incubated at 37° C. for 18 h. For identification of correct clones, plasmid DNA was isolated from the colonies obtained and the expression cassette was fully sequenced.

SEQ ID No. 28 specifies the amino acid sequence of the fusion protein TrxB5A resulting from the expression of the sequence SEQ ID No. 27.

Example 4: Enzyme Activity of the Cystine Reductases

For the recombinant expression of the proteins TrxA, TrxB, TrxBA, TrxB5A, TrxAB, and MI-TrxBA, the investigated expression plasmids encoding the corresponding protein were introduced into the strain *E. coli* TOP10 (Thermo Fisher Scientific, MA/USA). The bacterial cells were plated on LB medium containing 100 mg/L ampicillin. 25 ml of LB medium containing 100 mg/L ampicillin and 0.2% arabinose (w/v) was then inoculated with a single colony and incubated at 28° C. in a culture shaker cabinet for 18 h.

For the isolation of the expressed proteins, the cells were sedimented by centrifugation (10 min at 4000 g), the media supernatant was removed, and the biomass resuspended in lysis buffer (PBS+10% BugBuster (Sigma)). The cells were lysed completely in 15 min at RT as per the manufacturer's instructions in the manual of the BugBuster kit (Sigma) and then insoluble matter was removed by centrifugation (20 min at 9500 rpm as per the manufacturer's instructions). For purification of the supernatant (=cell lysate) by affinity chromatography, the cell lysate obtained was loaded into PBS-equilibrated Protino IDA2000 columns (Macherey & Nagel). After a wash step (7 ml of PBS), the samples were eluted with 5 ml of elution buffer (PBS+200 mM imidazole). The resulting protein concentrations were determined by a Bradford assay (Thermo Fisher).

The cystine reductase activity of the various enzymes TrxA, TrxB, TrxBA, TrxB5A, TrxAB or MI-TrxBA was determined using the two analytical methods described in detail below.

Figures 2, 3:
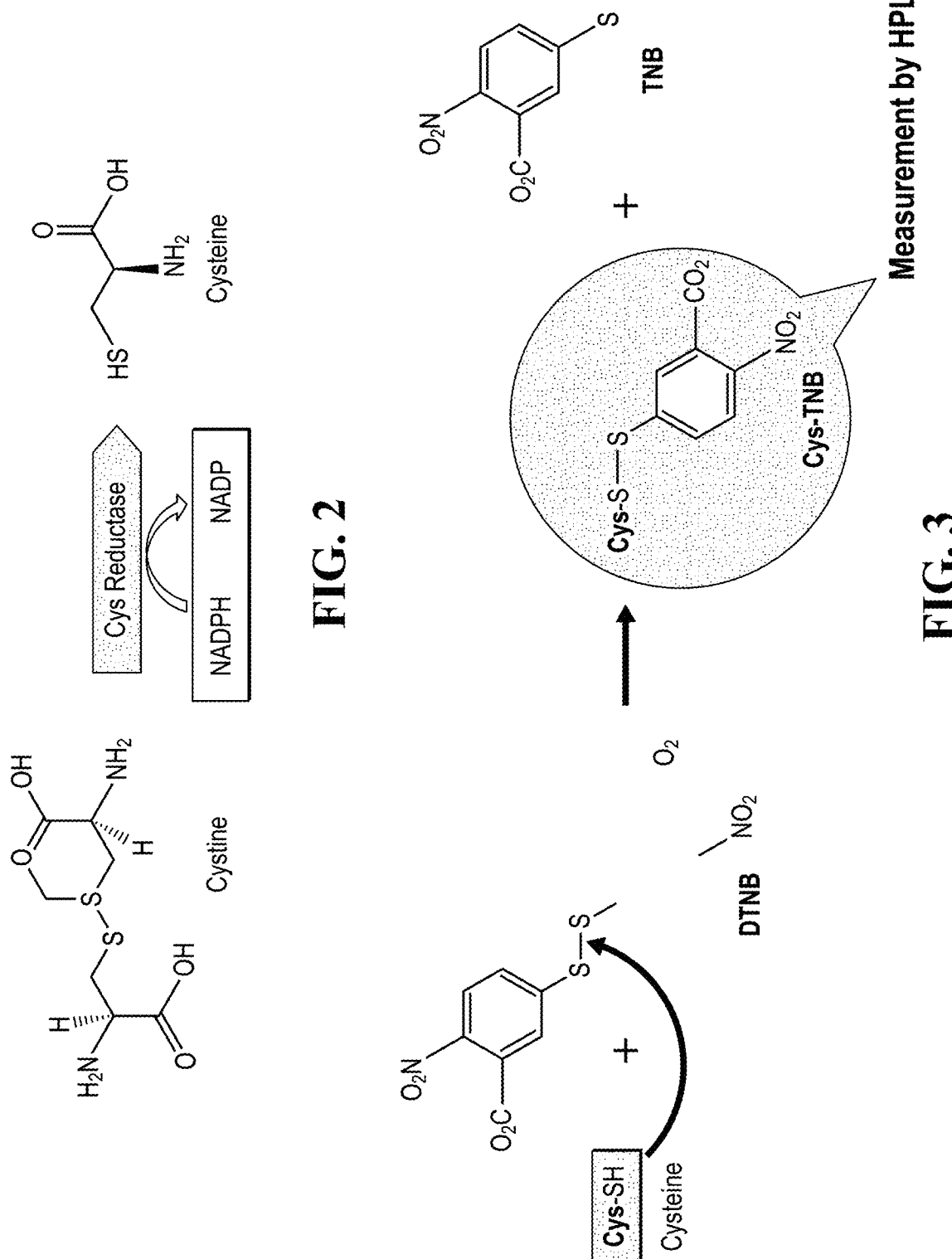
FIG. 2 shows a schematic illustration for the cystine reductase-catalyzed reduction of cystine to cysteine with oxidation of the cofactor NADPH to NADP+.
FIG. 3 a schematic illustration for the cystine reductase-catalyzed reduction of the combination of cysteine (Cys-SH) and DTNB (5,5'-dithiobis-2-nitrobenzoic acid; Ellman's reagent) with the release of Cys-TNB and TNB.

1. The first method consisted of the photometric detection method, which is based on the consumption of NADPH and the resulting fall in the absorbance values at 340 nm during the reduction reaction. As shown schematically in FIG. 2, the enzymatic conversion of cystine in the reduction to cysteine is accompanied by the consumption of the cofactor NADPH.

The following assay mixture was used for the photometric determination, the end volume of the samples being 1 ml:
   100 mM phosphate buffer pH 7.4
   2 mM EDTA
   0.2 mM NADPH (Sigma)
   1 mM cystine (Wacker Chemie AG)
   After mixing all assay components except for the enzyme, the reaction was started by adding the enzyme:
   10 μg of enzyme TrxA, TrxB, a mixture of TrxA and TrxB, TrxBA, TrxB5A, TrxAB or MI-TrxBA. The assay mixtures were incubated at room temperature (approx. 25° C.) until the measurement described below.

The NADPH concentration of the various 1 ml assay mixtures was measured at various times using a spectrophotometer (Evolution 201 UV-vis spectrophotometer, Thermo Fisher Scientific) in the form of absorbance values at 340 nm. The absorbance values at 340 nm were used to calculate the enzyme activity of the various samples using the Thermo INSIGHT software from the manufacturer Thermo Fisher Scientific. Analyzed in parallel in each case as negative controls were samples that contained either heat-inactivated enzyme, no enzyme, no cystine as substrate, or no NADPH as cofactor.

The enzyme activity was determined from the linear slope at the start of the recorded curve, with the change (decrease) in absorbance over time indicating the rate of NADPH consumption. Since the same amount of enzyme is always used, the rates can be compared.

2. In the second method, the cysteine formed from cystine by the cystine reductase activity was detected directly via the free SH group by reaction with the compound DTNB (5,5'-dithiobis-2-nitrobenzoic acid; Ellman's reagent), as shown schematically in FIG. 3, also referred to in the context of the present invention as the DTNB assay.

The following assay mixture was used for the photometric assay, the end volume of the samples being 1 ml:
   100 mM phosphate buffer pH 7.4
   2 mM EDTA
   0.2 mM NADPH (Sigma)
   1 mM cystine (Wacker Chemie AG)
   After mixing all assay components apart from the enzyme, the reaction was started by adding the enzyme:
   10 μg of enzyme TrxA, TrxB, a mixture of TrxA and TrxB, TrxBA, TrxB5A, TrxAB or MI-TrxBA. The assay mixtures were incubated at room temperature (approx. 25° C.) until the measurement described below.

L-Cysteine was quantified by the test described by Lee S.-H. et al. 1995 (Biochemical and Biophysical Research Communications 213, pp. 837-844) using 5,5'-dithiobis-2-nitrobenzoic acid (DTNB). Quantification of Cys-TNB was by measurement of the DTNB-mediated absorbance at 412 nm. Analysis by HPLC is also possible.

Analyzed in parallel in each case as negative controls were samples that contained either heat-inactivated enzyme, no enzyme, no cystine as substrate, or no NADPH as cofactor.

FIG. 4 shows the relative cystine reductase activity of the enzymes TrxBA, TrxB5A, TrxAB, and MI-Trx and of a (9:1) mixture of TrxA and TrxB according to photometric determination as described above under point 1, the activity of the (9:1) mixture of TrxA and TrxB being normalized to 1 and all other activities set in relation thereto. The (9:1) mixture of TrxA and TrxB is an estimated mixing ratio of the individual enzymes that comparative tests have shown to be the most active mixing ratio.

Figure 5:
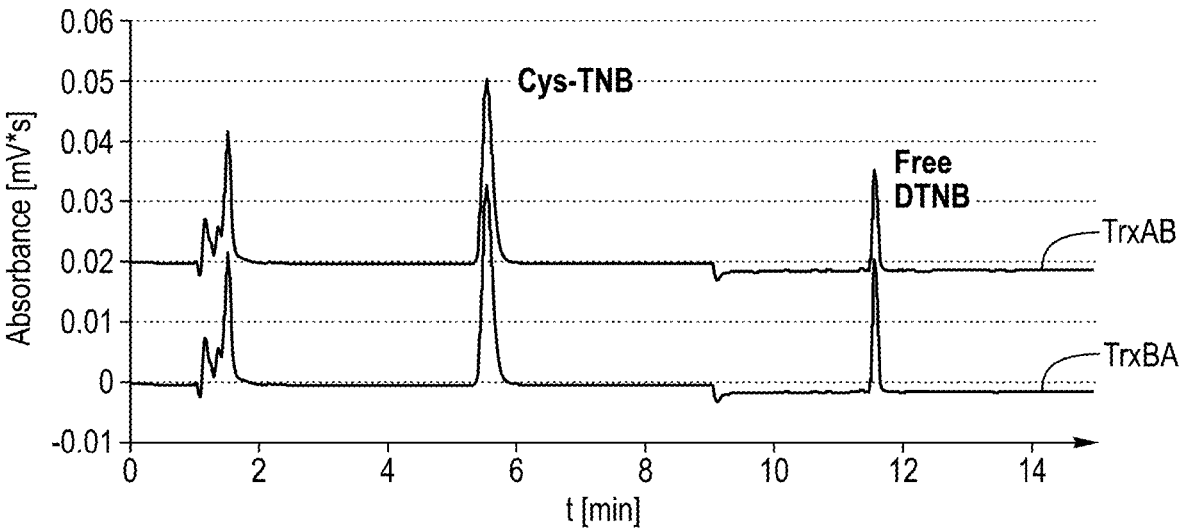
FIG. 5 shows chromatographic detection of cysteine formation by TrxBA and TrxAB using the DTNB assay.

FIG. 5 shows the detection of cysteine formation by TrxBA and TrxAB according to the DTNB assay and HPLC as described above under point 2.

The use of clones that contained a longer linker sequence than TrxB5A in the region of ≥60 nucleotides between the cds for TrxA and TrxB astonishingly led to significantly lower activity in the fusion protein.

Example 5: Activity of the Enzyme Combination Cystine Reductase and ADH

A comparison of the enzyme specificity toward the cofactors NADPH and NADP$^+$ found the cystine reductases TrxBA and TrxAB to be highly specific for the cofactor NADPH. In the tests, no enzyme activity toward cystine was detected with NADP$^+$. Combination experiments investigated the extent to which the enzyme alcohol dehydrogenase (ADH) is able to convert NADP$^+$ back into NADPH for the reaction.

The following conditions were used for this purpose:
100 mM phosphate buffer pH 7.4
5 μl of isopropanol
2 mM EDTA
15-50 μM NADPH or NADP$^+$
1 mM cystine
5 μg of enzyme TrxBA
50 μl of cell lysate crude extract or, as a negative control, 50 μl of phosphate buffer (Fast Prep digestion of 0.5 ml of cells in 1.5 ml of 4× phosphate buffer pH 7.4. Production of the cells as described in EP 1 832 658 B1)

The reaction was incubated at 30° C. for 60 min. Samples were taken at 5-minute intervals and the liberated cysteine was derivatized with DTNB as described in WO 2013/000864 A1. Quantification was by measurement of the DTNB-mediated absorbance at 412 nm.

Figure 6:
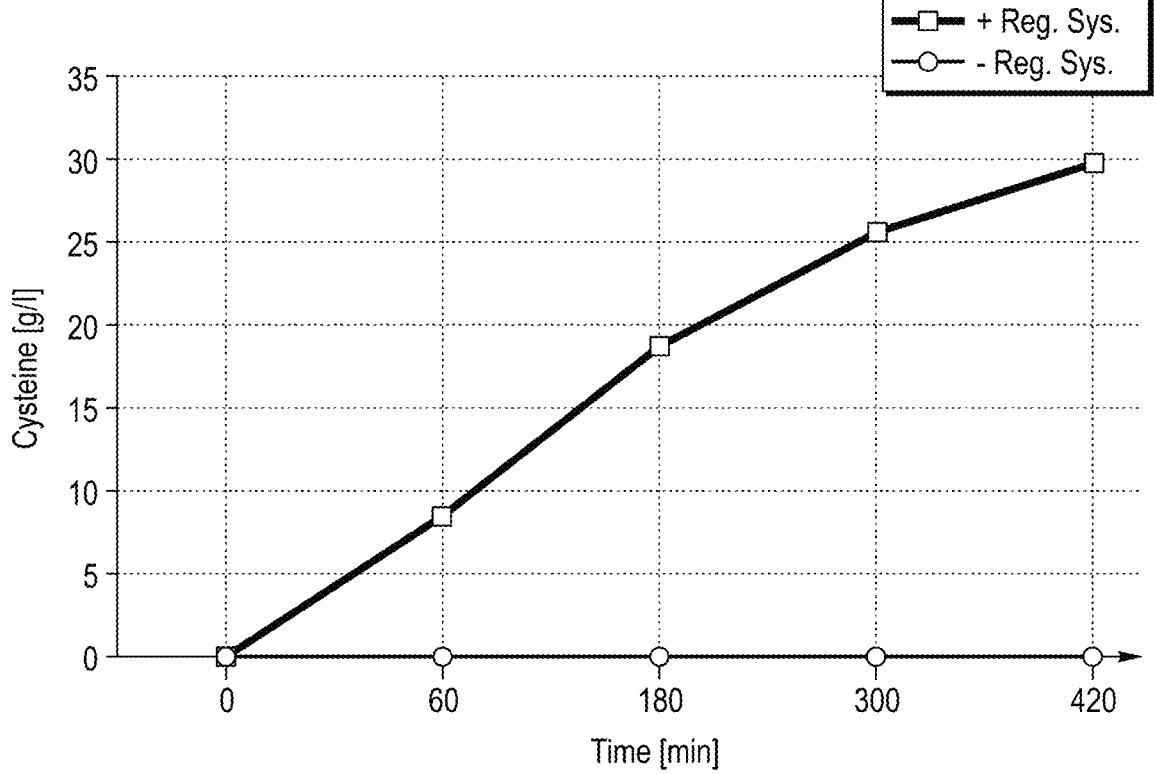
FIG. 6 shows the measurement of cysteine formation by TrxBA with and without regenerative system—measurement using the DTNB assay.

FIG. 6 shows the result of the measurement of cysteine formation by TrxBA using the DTNB assay in the presence (with) or absence (without) of ADH as a regenerative system.

Abbreviations Used in the Figures

AraC: AraC gene (repressor gene)
pAraC: Promoter of the AraC gene (repressor gene; rev orientation to P$_{BAD}$)
pBAD (in the context of the present invention referred to also as P$_{BAD}$): Arabinose-inducible promoter for expression (downstream) of inserted target protein sequences
6HIS: Coding region for His-tag
term: Transcription terminator
Amp: Ampicillin resistance marker
CR: Cystine reductase
rel.: Relative
bps: Base pairs
t: Time

---

The invention claimed is:

1. An enzyme for reducing cystine to cysteine, wherein the enzyme is a fusion protein that comprises the protein activities of i) thioredoxin (protein i) having the protein activity of thioredoxin 1 and ii) thioredoxin reductase (protein ii) having the protein activity of thioredoxin reductase, wherein the activity of the fusion protein is at least 100% of the activity of a mixture of the same but unfused individual proteins i and ii, wherein the fusion protein has the enzyme activity to reduce cystine to cysteine and wherein the coding sequence of protein i is located N-terminally or C-terminally with respect to the coding sequence of protein ii in the fusion protein, and wherein the fusion protein is an amino acid sequence selected from the group consisting of SEQ ID No. 9, SEQ ID No. 10, and SEQ ID No. 28.

2. A process for enzymatically reducing cystine to cysteine, wherein cystine is reduced by an enzyme as claimed in claim 1 in the presence of a cofactor, wherein two molecules of L-cysteine are formed from one molecule of the chemical compound cystine.

3. The process as claimed in claim 2, wherein the reduction takes place at a pH of from 6 to 9.

4. The process as claimed in claim 2, wherein the cofactor is a substance selected from the group consisting of NADPH and NADH.

5. The process as claimed in claim 2, wherein the process includes a cofactor-regenerating enzyme.

6. The process as claimed in claim 5, wherein the cofactor-regenerating enzyme is a dehydrogenase, with the reduction additionally taking place in the presence of an electron donor.

7. The process as claimed in claim 6, wherein the dehydrogenase is the alcohol dehydrogenase, with isopropanol used as the electron donor.

*    *    *    *    *

SEQUENCE LISTING

```
<160> NUMBER OF SEQ ID NOS: 30

<210> SEQ ID NO 1
<211> LENGTH: 36
<212> TYPE: DNA
<213> ORGANISM: artificial
<220> FEATURE:
<223> OTHER INFORMATION: his-tag

<400> SEQUENCE: 1
atgacacaga gggcccacca tcaccatcac cattcc                               36

<210> SEQ ID NO 2
<211> LENGTH: 330
<212> TYPE: DNA
<213> ORGANISM: Escherichia coli
<220> FEATURE:
<221> NAME/KEY: trxA
<222> LOCATION: (1)..(330)

<400> SEQUENCE: 2
atgagcgata aaattattca cctgactgac gacagttttg acacggatgt actcaaagcg      60
gacggggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggcgtaa                                     330

<210> SEQ ID NO 3
<211> LENGTH: 966
<212> TYPE: DNA
<213> ORGANISM: Escherichia coli
<220> FEATURE:
<221> NAME/KEY: trxB
<222> LOCATION: (1)..(966)

<400> SEQUENCE: 3
```

```
atgggcacga ccaaacacag taaactgctt atcctgggtt caggcccggc gggatacacc      60
gctgctgtct acgcggcgcg cgccaacctg caacctgtgc tgattaccgg catggaaaaa     120
ggcggccaac tgaccaccac cacggaagtg gaaaactggc ctggcgatcc aaacgatctg     180
accggtccgt tattaatgga gcgcatgcac gaacatgcca ccaagtttga aactgagatc     240
atttttgatc atatcaacaa ggtggatctg caaaaccgtc cgttccgtct gaatggcgat     300
aacggcgaat acacttgcga cgcgctgatt attgccaccg gagcttctgc acgctatctc     360
ggcctgccct ctgaagaagc ctttaaaggc cgtggggttt ctgcttgtgc aacctgcgac     420
ggtttcttct atcgcaacca gaaagttgcg gtcatcggcg cggcaatac cgcggttgaa     480 gaggcgctgt atctgtctaa catcgcttcg gaagtgcatc tgattcaccg ccgtgacggt     540
ttccgcgcgg aaaaaatcct cattaagcgc ctgatggata agtggagaa cggcaacatc      600 attctgcaca ccaaccgtac gctggaagaa gtgaccggcg atcaaatggg tgtcactggc     660
gttcgtctgc gcgatacgca aaacagcgat aacatcgagt cactcgacgt tgccggtctg     720
tttgttgcta tcggtcacag cccgaatact gcgattttcg aagggcagct ggaactggaa     780
aacggctaca tcaaagtaca gtcgggtatt catggtaatg ccacccagac cagcattcct     840
ggcgtctttg ccgcaggcga cgtgatggat cacatttatc gccaggccat tacttcggcc     900
ggtacaggct gcatggcagc acttgatgcg gaacgctacc tcgatggttt agctgacgca     960
aaataa                                                                966
```

```
<210> SEQ ID NO 4
<211> LENGTH: 1326
<212> TYPE: DNA
<213> ORGANISM: artificial
<220> FEATURE:
<223> OTHER INFORMATION: histrxAB (Fusion gene of his-tag and E.coli
      genes trxA and trxB)
<220> FEATURE:
<221> NAME/KEY: histrxAtrxB
<222> LOCATION: (1)..(1326)

<400> SEQUENCE: 4
```

```
atgacacaga gggcccacca tcaccatcac cattccatga gcgataaaat tattcacctg      60
actgacgaca gttttgacac ggatgtactc aaagcggacg gggcgatcct cgtcgatttc     120
tgggcagagt ggtgcggtcc gtgcaaaatg atcgccccga ttctggatga aatcgctgac     180
gaatatcagg gcaaactgac cgttgcaaaa ctgaacatcg atcaaaaccc tggcactgcg     240
ccgaaatatg gcatccgtgg tatcccgact ctgctgctgt tcaaaaacgg tgaagtggcg     300
gcaaccaaag tgggtgcact gtctaaaggt cagttgaaag agttcctcga cgctaacctg     360
gcgggcacga ccaaacacag taaactgctt atcctgggtt caggcccggc gggatacacc     420
gctgctgtct acgcggcgcg cgccaacctg caacctgtgc tgattaccgg catggaaaaa     480
ggcggccaac tgaccaccac cacggaagtg gaaaactggc ctggcgatcc aaacgatctg     540
accggtccgt tattaatgga gcgcatgcac gaacatgcca ccaagtttga aactgagatc     600
atttttgatc atatcaacaa ggtggatctg caaaaccgtc cgttccgtct gaatggcgat     660
aacggcgaat acacttgcga cgcgctgatt attgccaccg gagcttctgc acgctatctc     720
ggcctgccct ctgaagaagc ctttaaaggc cgtggggttt ctgcttgtgc aacctgcgac     780
ggtttcttct atcgcaacca gaaagttgcg gtcatcggcg cggcaatac cgcggttgaa     840 gaggcgctgt atctgtctaa catcgcttcg gaagtgcatc tgattcaccg ccgtgacggt     900
```

-continued

```
ttccgcgcgg aaaaaatcct cattaagcgc ctgatggata aagtggagaa cggcaacatc       960
attctgcaca ccaaccgtac gctggaagaa gtgaccggcg atcaaatggg tgtcactggc      1020
gttcgtctgc gcgatacgca aaacagcgat aacatcgagt cactcgacgt tgccggtctg      1080
tttgttgcta tcggtcacag cccgaatact gcgattttcg aagggcagct ggaactggaa      1140
aacggctaca tcaaagtaca gtcgggtatt catggtaatg ccacccagac cagcattcct      1200
ggcgtctttg ccgcaggcga cgtgatggat cacatttatc gccaggccat tacttcggcc      1260
ggtacaggct gcatggcagc acttgatgcg gaacgctacc tcgatggttt agctgacgca      1320
aaataa                                                                 1326

<210> SEQ ID NO 5
<211> LENGTH: 1326
<212> TYPE: DNA
<213> ORGANISM: artificial
<220> FEATURE:
<223> OTHER INFORMATION: histrxBA (Fusion  gene of his-tag and E.coli
      genes trxB and trxA)
<220> FEATURE:
<221> NAME/KEY: histrxBtrxA
<222> LOCATION: (1)..(1326)

<400> SEQUENCE: 5
atgacacaga gggcccacca tcaccatcac cattccatgg gcacgaccaa acacagtaaa        60
ctgcttatcc tgggttcagg cccggcggga tacaccgctg ctgtctacgc ggcgcgcgcc       120
aacctgcaac ctgtgctgat taccggcatg gaaaaaggcg ccaactgac caccaccacg        180 gaagtggaaa actggcctgg cgatccaaac gatctgaccg tccgttatt aatggagcgc        240 atgcacgaac atgccaccaa gtttgaaact gagatcattt ttgatcatat caacaaggtg       300
gatctgcaaa accgtccgtt ccgtctgaat ggcgataacg cgaatacac ttgcgacgcg        360 ctgattattg ccaccggagc ttctgcacgc tatctcggcc tgccctctga gaagcctttt      420
aaaggccgtg gggtttctgc ttgtgcaacc tgcgacggtt tcttctatcg caaccagaaa       480
gttgcggtca tcggcggcgg caataccgcg gttgaagagg cgctgtatct gtctaacatc       540
gcttcggaag tgcatctgat tcaccgccgt gacggtttcc gcgcggaaaa aatcctcatt       600
aagcgcctga tggataaagt ggagaacggc aacatcattc tgcacaccaa ccgtacgctg       660
gaagaagtga ccggcgatca aatgggtgtc actggcgttc gtctgcgcga tacgcaaaac       720
agcgataaca tcgagtcact cgacgttgcc ggtctgtttg ttgctatcgg tcacagcccg       780
aatactgcga ttttcgaagg gcagctggaa ctggaaaacg gctacatcaa agtacagtcg       840
ggtattcatg gtaatgccac ccagaccagc attcctggcg tctttgccgc aggcgacgtg       900
atggatcaca tttatcgcca ggccattact tcggccggta caggctgcat ggcagcactt       960
gatgcggaac gctacctcga tggtttagct gacgcaggta gcgataaaat tattcacctg      1020
actgacgaca gttttgacac ggatgtactc aaagcggacg gggcgatcct cgtcgatttc      1080
tgggcagagt ggtgcggtcc gtgcaaaatg atcgccccga ttctggatga aatcgctgac      1140
gaatatcagg gcaaactgac cgttgcaaaa ctgaacatcg atcaaaaccc tggcactgcg      1200
ccgaaatatg gcatccgtgg tatcccgact ctgctgctgt tcaaaaacgg tgaagtggcg      1260
gcaaccaaag tgggtgcact gtctaaaggt cagttgaaag agttcctcga cgctaacctg      1320
gcgtaa                                                                 1326

<210> SEQ ID NO 6
<211> LENGTH: 12
```

-continued

```
<212> TYPE: PRT
<213> ORGANISM: artificial
<220> FEATURE:
<223> OTHER INFORMATION: His-tag
<220> FEATURE:
<221> NAME/KEY: His-tag
<222> LOCATION: (1)..(12)

<400> SEQUENCE: 6

Met Thr Gln Arg Ala His His His His His His Ser
1               5                   10

<210> SEQ ID NO 7
<211> LENGTH: 109
<212> TYPE: PRT
<213> ORGANISM: Escherichia coli
<220> FEATURE:
<221> NAME/KEY: TrxA
<222> LOCATION: (1)..(109)

<400> SEQUENCE: 7

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105

<210> SEQ ID NO 8
<211> LENGTH: 321
<212> TYPE: PRT
<213> ORGANISM: Escherichia coli
<220> FEATURE:
<221> NAME/KEY: TrxB
<222> LOCATION: (1)..(321)

<400> SEQUENCE: 8

Met Gly Thr Thr Lys His Ser Lys Leu Leu Ile Leu Gly Ser Gly Pro
1               5                   10                  15

Ala Gly Tyr Thr Ala Ala Val Tyr Ala Ala Arg Ala Asn Leu Gln Pro
            20                  25                  30

Val Leu Ile Thr Gly Met Glu Lys Gly Gly Gln Leu Thr Thr Thr Thr
            35                  40                  45

Glu Val Glu Asn Trp Pro Gly Asp Pro Asn Asp Leu Thr Gly Pro Leu
        50                  55                  60

Leu Met Glu Arg Met His Glu His Ala Thr Lys Phe Glu Thr Glu Ile
65                  70                  75                  80

Ile Phe Asp His Ile Asn Lys Val Asp Leu Gln Asn Arg Pro Phe Arg
                85                  90                  95

Leu Asn Gly Asp Asn Gly Glu Tyr Thr Cys Asp Ala Leu Ile Ile Ala
            100                 105                 110

Thr Gly Ala Ser Ala Arg Tyr Leu Gly Leu Pro Ser Glu Glu Ala Phe
            115                 120                 125
```

```
Lys Gly Arg Gly Val Ser Ala Cys Ala Thr Cys Asp Gly Phe Phe Tyr
    130                 135                 140

Arg Asn Gln Lys Val Ala Val Ile Gly Gly Gly Asn Thr Ala Val Glu
145                 150                 155                 160

Glu Ala Leu Tyr Leu Ser Asn Ile Ala Ser Glu Val His Leu Ile His
                165                 170                 175

Arg Arg Asp Gly Phe Arg Ala Glu Lys Ile Leu Ile Lys Arg Leu Met
                180                 185                 190

Asp Lys Val Glu Asn Gly Asn Ile Ile Leu His Thr Asn Arg Thr Leu
            195                 200                 205

Glu Glu Val Thr Gly Asp Gln Met Gly Val Thr Gly Val Arg Leu Arg
    210                 215                 220

Asp Thr Gln Asn Ser Asp Asn Ile Glu Ser Leu Asp Val Ala Gly Leu
225                 230                 235                 240

Phe Val Ala Ile Gly His Ser Pro Asn Thr Ala Ile Phe Glu Gly Gln
                245                 250                 255

Leu Glu Leu Glu Asn Gly Tyr Ile Lys Val Gln Ser Gly Ile His Gly
            260                 265                 270

Asn Ala Thr Gln Thr Ser Ile Pro Gly Val Phe Ala Ala Gly Asp Val
            275                 280                 285

Met Asp His Ile Tyr Arg Gln Ala Ile Thr Ser Ala Gly Thr Gly Cys
    290                 295                 300

Met Ala Ala Leu Asp Ala Glu Arg Tyr Leu Asp Gly Leu Ala Asp Ala
305                 310                 315                 320

Lys
```

```
<210> SEQ ID NO 9
<211> LENGTH: 441
<212> TYPE: PRT
<213> ORGANISM: artificial
<220> FEATURE:
<223> OTHER INFORMATION: HisTrxAB (Fusion protein of His-tag and E.coli
      protein TrxA and TrxB)
<220> FEATURE:
<221> NAME/KEY: HisTrxAB
<222> LOCATION: (1)..(441)

<400> SEQUENCE: 9
```

```
Met Thr Gln Arg Ala His His His His His His Ser Met Ser Asp Lys
1               5                   10                  15

Ile Ile His Leu Thr Asp Asp Ser Phe Asp Thr Asp Val Leu Lys Ala
                20                  25                  30

Asp Gly Ala Ile Leu Val Asp Phe Trp Ala Glu Trp Cys Gly Pro Cys
            35                  40                  45

Lys Met Ile Ala Pro Ile Leu Asp Glu Ile Ala Asp Glu Tyr Gln Gly
    50                  55                  60

Lys Leu Thr Val Ala Lys Leu Asn Ile Asp Gln Asn Pro Gly Thr Ala
65                  70                  75                  80

Pro Lys Tyr Gly Ile Arg Gly Ile Pro Thr Leu Leu Leu Phe Lys Asn
                85                  90                  95

Gly Glu Val Ala Ala Thr Lys Val Gly Ala Leu Ser Lys Gly Gln Leu
                100                 105                 110

Lys Glu Phe Leu Asp Ala Asn Leu Ala Gly Thr Thr Lys His Ser Lys
            115                 120                 125

Leu Leu Ile Leu Gly Ser Gly Pro Ala Gly Tyr Thr Ala Ala Val Tyr
    130                 135                 140
```

-continued

```
Ala Ala Arg Ala Asn Leu Gln Pro Val Leu Ile Thr Gly Met Glu Lys
145                 150                 155                 160

Gly Gly Gln Leu Thr Thr Thr Thr Glu Val Glu Asn Trp Pro Gly Asp
                165                 170                 175

Pro Asn Asp Leu Thr Gly Pro Leu Leu Met Glu Arg Met His Glu His
            180                 185                 190

Ala Thr Lys Phe Glu Thr Glu Ile Ile Phe Asp His Ile Asn Lys Val
            195                 200                 205

Asp Leu Gln Asn Arg Pro Phe Arg Leu Asn Gly Asp Asn Gly Glu Tyr
        210                 215                 220

Thr Cys Asp Ala Leu Ile Ile Ala Thr Gly Ala Ser Ala Arg Tyr Leu
225                 230                 235                 240

Gly Leu Pro Ser Glu Glu Ala Phe Lys Gly Arg Gly Val Ser Ala Cys
                245                 250                 255

Ala Thr Cys Asp Gly Phe Phe Tyr Arg Asn Gln Lys Val Ala Val Ile
            260                 265                 270

Gly Gly Gly Asn Thr Ala Val Glu Glu Ala Leu Tyr Leu Ser Asn Ile
            275                 280                 285

Ala Ser Glu Val His Leu Ile His Arg Arg Asp Gly Phe Arg Ala Glu
        290                 295                 300

Lys Ile Leu Ile Lys Arg Leu Met Asp Lys Val Glu Asn Gly Asn Ile
305                 310                 315                 320

Ile Leu His Thr Asn Arg Thr Leu Glu Glu Val Thr Gly Asp Gln Met
                325                 330                 335

Gly Val Thr Gly Val Arg Leu Arg Asp Thr Gln Asn Ser Asp Asn Ile
            340                 345                 350

Glu Ser Leu Asp Val Ala Gly Leu Phe Val Ala Ile Gly His Ser Pro
        355                 360                 365

Asn Thr Ala Ile Phe Glu Gly Gln Leu Glu Leu Glu Asn Gly Tyr Ile
        370                 375                 380

Lys Val Gln Ser Gly Ile His Gly Asn Ala Thr Gln Thr Ser Ile Pro
385                 390                 395                 400

Gly Val Phe Ala Ala Gly Asp Val Met Asp His Ile Tyr Arg Gln Ala
                405                 410                 415

Ile Thr Ser Ala Gly Thr Gly Cys Met Ala Ala Leu Asp Ala Glu Arg
            420                 425                 430

Tyr Leu Asp Gly Leu Ala Asp Ala Lys
        435                 440
```

```
<210> SEQ ID NO 10
<211> LENGTH: 441
<212> TYPE: PRT
<213> ORGANISM: artificial
<220> FEATURE:
<223> OTHER INFORMATION: HisTrxBA (Fusion protein of His-tag and E.coli
      proteins TrxB and TrxA)
<220> FEATURE:
<221> NAME/KEY: His-TrxBA
<222> LOCATION: (1)..(441)

<400> SEQUENCE: 10
```

```
Met Thr Gln Arg Ala His His His His His His Ser Met Gly Thr Thr
1                   5                   10                  15

Lys His Ser Lys Leu Leu Ile Leu Gly Ser Gly Pro Ala Gly Tyr Thr
                20                  25                  30

Ala Ala Val Tyr Ala Ala Arg Ala Asn Leu Gln Pro Val Leu Ile Thr
```

-continued

```
              35                  40                  45
Gly Met Glu Lys Gly Gly Gln Leu Thr Thr Thr Thr Glu Val Glu Asn
     50                  55                  60

Trp Pro Gly Asp Pro Asn Asp Leu Thr Gly Pro Leu Leu Met Glu Arg
65                  70                  75                  80

Met His Glu His Ala Thr Lys Phe Glu Thr Glu Ile Ile Phe Asp His
                85                  90                  95

Ile Asn Lys Val Asp Leu Gln Asn Arg Pro Phe Arg Leu Asn Gly Asp
               100                 105                 110

Asn Gly Glu Tyr Thr Cys Asp Ala Leu Ile Ile Ala Thr Gly Ala Ser
               115                 120                 125

Ala Arg Tyr Leu Gly Leu Pro Ser Glu Glu Ala Phe Lys Gly Arg Gly
           130                 135                 140

Val Ser Ala Cys Ala Thr Cys Asp Gly Phe Phe Tyr Arg Asn Gln Lys
145                 150                 155                 160

Val Ala Val Ile Gly Gly Gly Asn Thr Ala Val Glu Glu Ala Leu Tyr
               165                 170                 175

Leu Ser Asn Ile Ala Ser Glu Val His Leu Ile His Arg Arg Asp Gly
               180                 185                 190

Phe Arg Ala Glu Lys Ile Leu Ile Lys Arg Leu Met Asp Lys Val Glu
           195                 200                 205

Asn Gly Asn Ile Ile Leu His Thr Asn Arg Thr Leu Glu Glu Val Thr
           210                 215                 220

Gly Asp Gln Met Gly Val Thr Gly Val Arg Leu Arg Asp Thr Gln Asn
225                 230                 235                 240

Ser Asp Asn Ile Glu Ser Leu Asp Val Ala Gly Leu Phe Val Ala Ile
               245                 250                 255

Gly His Ser Pro Asn Thr Ala Ile Phe Glu Gly Gln Leu Glu Leu Glu
               260                 265                 270

Asn Gly Tyr Ile Lys Val Gln Ser Gly Ile His Gly Asn Ala Thr Gln
           275                 280                 285

Thr Ser Ile Pro Gly Val Phe Ala Ala Gly Asp Val Met Asp His Ile
           290                 295                 300

Tyr Arg Gln Ala Ile Thr Ser Ala Gly Thr Gly Cys Met Ala Ala Leu
305                 310                 315                 320

Asp Ala Glu Arg Tyr Leu Asp Gly Leu Ala Asp Ala Gly Ser Asp Lys
               325                 330                 335

Ile Ile His Leu Thr Asp Asp Ser Phe Asp Thr Asp Val Leu Lys Ala
               340                 345                 350

Asp Gly Ala Ile Leu Val Asp Phe Trp Ala Glu Trp Cys Gly Pro Cys
           355                 360                 365

Lys Met Ile Ala Pro Ile Leu Asp Glu Ile Ala Asp Glu Tyr Gln Gly
           370                 375                 380

Lys Leu Thr Val Ala Lys Leu Asn Ile Asp Gln Asn Pro Gly Thr Ala
385                 390                 395                 400

Pro Lys Tyr Gly Ile Arg Gly Ile Pro Thr Leu Leu Leu Phe Lys Asn
               405                 410                 415

Gly Glu Val Ala Ala Thr Lys Val Gly Ala Leu Ser Lys Gly Gln Leu
               420                 425                 430

Lys Glu Phe Leu Asp Ala Asn Leu Ala
           435                 440
```

<210> SEQ ID NO 11

-continued

```
<211> LENGTH: 4100
<212> TYPE: DNA
<213> ORGANISM: artificial
<220> FEATURE:
<223> OTHER INFORMATION: pGJ3477 (vector sequence)
<220> FEATURE:
<221> NAME/KEY: pGJ3477
<222> LOCATION: (1)..(4100)

<400> SEQUENCE: 11
aaaccaattg tccatattgc atcagacatt gccgtcactg cgtcttttac tggctcttct       60
cgctaaccaa accggtaacc ccgcttatta aaagcattct gtaacaaagc gggaccaaag      120
ccatgacaaa aacgcgtaac aaaagtgtct ataatcacgg cagaaaagtc cacattgatt      180
atttgcacgg cgtcacactt tgctatgcca tagcattttt atccataaga ttagctgatc      240
ctacctgacg cttttttatcg caactctcta ctgtttctcc atacccgttt aaataatttt      300
gtttaacttt aagaaggaga tatacccatg acacagaggg cccaccatca ccatcaccat      360
tccggatccg gctgctaaca aagcccgaaa ggaagctgag ttggctgctg ccaccgctga      420
gcaataacta gcataacccc ttggggcctc taaacgggtc ttgaggggtt ttttgctgaa      480
aggaggaact atatccggcc ggatatccac aggacgggtg tggtcgccat gatcgcgtag      540
tcgatagtgg ctccaagtag cgaagcgagc aggactgggc ggcggccaaa gcggtcggac      600
agtgctccga gaacgggtgc gcatagaaat tgcatcaacg catatagcgc tagcagcacg      660
ccatagtgac tggcgatgct gtcggaatgg acgatatccc gcaagaggcc cggcagtacc      720
ggcataacca agcctatgcc tacagcatcc agggtgacgg tgccgaggat gacgatgagc      780
gcattgttag atttcataca cggtgcctga ctgcgttagc aatttaactg tgataaacta      840
ccgcattaaa gcttatcgat gataagctgt caaacatgag aattcttgaa gacgaaaggg      900
cctcgtgata cgcctatttt tataggttaa tgtcatgcat gagacaataa ccctgataaa      960
tgcttcaata atattgaaaa aggaagagta tgagtattca acatttccgt gtcgccctta     1020
ttcccttttt tgcggcattt tgccttcctg tttttgctca cccagaaacg ctggtgaaag     1080
taaaagatgc tgaagatcag ttgggtgcac gagtgggtta catcgaactg gatctcaaca     1140
gcggtaagat ccttgagagt tttcgccccg aagaacgttt tccaatgatg agcacttta     1200 aagttctgct atgtggcgcg gtattatccc gtgttgacgc cgggcaagag caactcggtc     1260
gccgcataca ctattctcag aatgacttgg ttgacgcgtc accagtcaca gaaaagcatc     1320
ttacggatgg catgacagta agagaattat gcagtgctgc cataaccatg agtgataaca     1380
ctgcggccaa cttacttctg acaacgatcg gaggaccgaa ggagctaacc gcttttttgc     1440
acaacatggg ggatcatgta actcgccttg atcgttggga accggagctg aatgaagcca     1500
taccaaacga cgagcgtgac accacgatgc ctgcagcaat ggcaacaacg ttgcgcaaac     1560
tattaactgg cgaactactt actctagctt cccggcaaca attaatagac tggatggagg     1620
cggataaagt tgcaggacca cttctgcgct cggcccttcc ggctggctgg tttattgctg     1680
ataaatctgg agccggtgag cgtgggtctc gcggtatcat tgcagcactg gggccagatg     1740
gtaagccctc ccgtatcgta gttatctaca cgacggggag tcaggcaact atggatgaac     1800
gaaatagaca gatcgctgag ataggtgcct cactgattaa gcattggtaa ctgtcagacc     1860
aagtttactc atatatactt tagattgatt taaaacttca tttttaattt aaaaggatct     1920
aggtgaagat cctttttgat aatctcatgc atgaccaaaa tcccttaacg tgagttttcg     1980
ttccactgag cgtcagaccc cgtagaaaag atcaaaggat cttcttgaga tcctttttttt     2040
```

-continued

```
ctgcgcgtaa tctgctgctt gcaaacaaaa aaaccaccgc taccagcggt ggtttgtttg      2100
ccggatcaag agctaccaac tcttttttccg aaggtaactg gcttcagcag agcgcagata     2160
ccaaatactg tccttctagt gtagccgtag ttaggccacc acttcaagaa ctctgtagca      2220
ccgcctacat acctcgctct gctaatcctg ttaccagtgg ctgctgccag tggcgataag      2280
tcgtgtctta ccgggttgga ctcaagacga tagttaccgg ataaggcgca gcggtcgggc      2340
tgaacggggg gttcgtgcac acagcccagc ttggagcgaa cgacctacac cgaactgaga      2400
tacctacagc gtgagctatg agaaagcgcc acgcttcccg aagggagaaa ggcggacagg      2460
tatccggtaa gcggcagggt cggaacagga gagcgcacga gggagcttcc aggggggaaac     2520 gcctggtatc tttatagtcc tgtcgggttt cgccacctct gacttgagcg tcgattttg      2580 tgatgctcgt cagggggggcg gagcctatgg aaaaacgcca gcaacgcggc cttttttacgg   2640 ttcctggcct tttgctggcc ttttgctcac atgttctttc ctgcgttatc ccctgattct      2700
gtggataacc gtattaccgc ctttgagtga gctgataccg ctcgccgcag ccgaacgacc      2760
gagcgcagcg agtcagtgag cgaggaagcg gaagagcgcc tgatgcggta ttttctcctt      2820
acgcatctgt gcggtatttc acaccgcata tatggtgcac tctcagtaca atctgctctg      2880
atgccgcata gttaagccag tatacactcc gctatcgcta cgtgactggg tcatggctgc      2940
gccccgacac ccgccaacac ccgctgacgc gccctgacgg gcttgtctgc tcccggcatc      3000
cgcttacaga caagctgtga ccgtctccgg gagctgcatg tgtcagaggt tttcaccgtc      3060
atcaccgaaa cgcgcgaggc agctggcacg acaggtttcc cgactggaat gtgcctgtca      3120
aatggacgaa gcagggattc tgcaaaccct atgctactcc gtcaagccgt caattgtctg      3180
attcgttacc aattatgaca acttgacggc tacatcattc acttttttctt cacaaccggc     3240 acggaactcg ctcgggctgg ccccggtgca tttttttaaat acccgcgaga aatagagttg     3300
atcgtcaaaa ccaacattgc gaccgacggt ggcgataggc atccgggtgg tgctcaaaag     3360
cagcttcgcc tggctgatac gttggtcctc gcgccagctt aagacgctaa tccctaactg      3420
ctggcggaaa agatgtgaca gacgcgacgg cgacaagcaa acatgctgtg cgacgctggc      3480
gatatcaaaa ttgctgtctg ccaggtgatc gctgatgtac tgacaagcct cgcgtacccg      3540
attatccatc ggtggatgga gcgactcgtt aatcgcttcc atgcgccgca gtaacaattg      3600
ctcaagcaga tttatcgcca gcagctccga atagcgccct tccccttgcc cggcgttaat      3660
gatttgccca aacaggtcgc tgaaatgcgg ctggtgcgct tcatccgggc gaaagaaccc      3720
cgtattggca aatattgacg gccagttaag ccattcatgc cagtaggcgc gcggacgaaa      3780
gtaaacccac tggtgatacc attcgcgagc ctccggatga cgaccgtagt gatgaatctc      3840
tcctggcggg aacagcaaaa tatcacccgg tcggcaaaca aattctcgtc cctgattttt      3900 caccacccccc tgaccgcgaa tggtgagatt gagaatataa cctttcattc ccagcggtcg     3960
gtcgataaaa aaatcgagat aaccgttggc ctcaatcggc gttaaacccg ccaccagatg      4020
ggcattaaac gagtatcccg gcagcagggg atcattttgc gcttcagcca tacttttcat      4080
actcccgcca ttcagagaag                                                  4100
```

<210> SEQ ID NO 12
<211> LENGTH: 21
<212> TYPE: DNA
<213> ORGANISM: artificial
<220> FEATURE:
<223> OTHER INFORMATION: 3477 - fwrd (Primer sequence vector pGJ3477-
     fwrd)
<220> FEATURE:

```
<221> NAME/KEY: 3477-fwrd
<222> LOCATION: (1)..(21)

<400> SEQUENCE: 12
ggatccggct gctaacaaag c                                             21

<210> SEQ ID NO 13
<211> LENGTH: 21
<212> TYPE: DNA
<213> ORGANISM: artificial
<220> FEATURE:
<223> OTHER INFORMATION: 3477 - rev (Primer sequence vector pGJ3477-rev)
<220> FEATURE:
<221> NAME/KEY: 3477-rev
<222> LOCATION: (1)..(21)

<400> SEQUENCE: 13
ggaatggtga tggtgatggt g                                             21

<210> SEQ ID NO 14
<211> LENGTH: 48
<212> TYPE: DNA
<213> ORGANISM: artificial
<220> FEATURE:
<223> OTHER INFORMATION: trxA-fwrd (Primer sequence trxA-fwrd)
<220> FEATURE:
<221> NAME/KEY: trxA-fwrd
<222> LOCATION: (1)..(48)

<400> SEQUENCE: 14
catcaccatc accattccat gagcgataaa attattcacc tgactgac                48

<210> SEQ ID NO 15
<211> LENGTH: 45
<212> TYPE: DNA
<213> ORGANISM: artificial
<220> FEATURE:
<223> OTHER INFORMATION: trxA-rev (Primer sequence trxA-rev)
<220> FEATURE:
<221> NAME/KEY: trxA-rev
<222> LOCATION: (1)..(45)

<400> SEQUENCE: 15
ctttgttagc agccggatcc ttacgccagg ttagcgtcga ggaac                   45

<210> SEQ ID NO 16
<211> LENGTH: 40
<212> TYPE: DNA
<213> ORGANISM: artificial
<220> FEATURE:
<223> OTHER INFORMATION: trxB-fwrd (Primer sequence trxB-fwrd)
<220> FEATURE:
<221> NAME/KEY: trxB-fwrd
<222> LOCATION: (1)..(40)

<400> SEQUENCE: 16
caccatcacc attccatggg cacgaccaaa cacagtaaac                         40

<210> SEQ ID NO 17
<211> LENGTH: 47
<212> TYPE: DNA
<213> ORGANISM: artificial
<220> FEATURE:
<223> OTHER INFORMATION: trxB-rev (Primer sequence trxB-rev)
<220> FEATURE:
<221> NAME/KEY: trxB-rev
<222> LOCATION: (1)..(47)

<400> SEQUENCE: 17
```

-continued ctttgttagc agccggatcc ttattttgcg tcagctaaac catcgag                47

<210> SEQ ID NO 18
<211> LENGTH: 38
<212> TYPE: DNA
<213> ORGANISM: artificial
<220> FEATURE:
<223> OTHER INFORMATION: vtrxA-fwrd (Primer vector with trxA for trxBA
      fusion gene fwrd)
<220> FEATURE:
<221> NAME/KEY: vtrxA-fwrd
<222> LOCATION: (1)..(38)

<400> SEQUENCE: 18
ctgacgcagg tagcgataaa attattcacc tgactgac                38

<210> SEQ ID NO 19
<211> LENGTH: 46
<212> TYPE: DNA
<213> ORGANISM: artificial
<220> FEATURE:
<223> OTHER INFORMATION: ftrxB-fwrd (Primer insert trxB for trxBA fusion
      gene fwrd)
<220> FEATURE:
<221> NAME/KEY: ftrxB-fwrd
<222> LOCATION: (1)..(46)

<400> SEQUENCE: 19
catcaccatc accattccat gggcacgacc aaacacagta aactgc                46

<210> SEQ ID NO 20
<211> LENGTH: 52
<212> TYPE: DNA
<213> ORGANISM: artificial
<220> FEATURE:
<223> OTHER INFORMATION: ftrxB-rev (Primer insert trxB for trxBA fusion
      gene rev)
<220> FEATURE:
<221> NAME/KEY: ftrxB-rev
<222> LOCATION: (1)..(52)

<400> SEQUENCE: 20
gtcaggtgaa taattttatc gctacctgcg tcagctaaac catcgaggta gc                52

<210> SEQ ID NO 21
<211> LENGTH: 37
<212> TYPE: DNA
<213> ORGANISM: artificial
<220> FEATURE:
<223> OTHER INFORMATION: vtrxB-fwrd (Primer vector with trxB for trxAB
      fusion gene fwrd)
<220> FEATURE:
<221> NAME/KEY: vtrxB-fwrd
<222> LOCATION: (1)..(37)

<400> SEQUENCE: 21
cgctaacctg gcgggcacga ccaaacacag taaactg                37

<210> SEQ ID NO 22
<211> LENGTH: 48
<212> TYPE: DNA
<213> ORGANISM: artificial
<220> FEATURE:
<223> OTHER INFORMATION: ftrxA-fwrd (Primer insert trxA for trxAB fusion
      gene fwrd)
<220> FEATURE:
<221> NAME/KEY: ftrxA-fwrd
<222> LOCATION: (1)..(48)

-continued

```
<400> SEQUENCE: 22
catcaccatc accattccat gagcgataaa attattcacc tgactgac                48

<210> SEQ ID NO 23
<211> LENGTH: 37
<212> TYPE: DNA
<213> ORGANISM: artificial
<220> FEATURE:
<223> OTHER INFORMATION: ftrxA-rev (Primer insert trxA for trxAB fusion
      gene rev)
<220> FEATURE:
<221> NAME/KEY: ftrxA-rev
<222> LOCATION: (1)..(37)

<400> SEQUENCE: 23
gtgtttggtc gtgcccgcca ggttagcgtc gaggaac                            37

<210> SEQ ID NO 24
<211> LENGTH: 1377
<212> TYPE: DNA
<213> ORGANISM: artificial
<220> FEATURE:
<223> OTHER INFORMATION: Ml-trxBA (E.coli codon usage optimized ml-trxBA
      gene)
<220> FEATURE:
<221> NAME/KEY: Ml-trxBA
<222> LOCATION: (1)..(1377)

<400> SEQUENCE: 24
atgaacacaa cgcctagtgc gcatgagaca atccatgaag tgatcgtcat aggttccggt       60
cctgcgggtt atacagcagc gttgtacgca gctagagcac aactgacccc tctcgtcttt      120
gagggcacat catttggcgg ggctttaatg accacaactg aagtcgagaa ctacccgggt      180
tttcgcaacg gtattacagg tccggaactc atggacgaca tgcgtgaaca ggcattacgg      240
tttggagcgg agctgcgtac cgaagatgtt gagtcagtca gtctaagagg accgataaaa      300
tccgttgtca ctgccgaggg ccagacctat caagcgagag cggtgattct ggctatggga      360
acttctgtac gttacttaca aataccgggt gagcaggaac tgctcgggcg cggagtgtcc      420
gcttgcgcga cctgtgatgg tagtttcttc aggggccaag atatcgccgt gatcggtggt      480
ggcgacagcg ctatggagga agcgctgttt cttacccgat tcgccagatc tgtgactctc      540
gtacaccgac gcgacgagtt tcgtgcgagt aaaatcatgt tgggtcgcgc ccgtaataac      600
gataaaataa agttcataac taaccacacg gtggtggcag tcaatggcta taccacggtg      660
accggactgc gtttgcggaa tacgacgacc ggtgaagaaa ccacattagt cgtaaccggc      720
gtcttcgtgg ctattggcca cgaaccgaga agttctttag tgtcagatgt agtggatata      780
gatcccgacg gttatgtact ggtaaagggt cgaactactt ccaccagcat ggatggagtg      840
ttcgcggctg gggacttggt tgaccgcaca tatcgtcaag caattaccgc tgcgggttca      900
ggctgcgctg cggctataga cgcggaacgt tggttggcag agcatgcggg ttccaaggca      960
aatgaaacca ctgaagagac aggcgacgtg gattccaccg atacgacaga ttggtccaca     1020
gcgatgacag acgcaaagaa tgctggtgtg actatcgagg ttacggacgc ctctttcttc     1080
gccgacgttc taagctcaaa taagccggtc tcgtcgact tctgggccac ttggtgtggc     1140
ccgtgtaaaa tggttgcacc cgtgttagag gagattgcat cggaacagcg caatcaatta     1200
acagttgcta agcttgatgt cgatacgaac ccgagatgg ctagagagtt tcaggtcgtg     1260 tccatacctta caatgatatt atttcaaggt ggtcaaccgg tcaagcgcat cgtaggggcg     1320
aaagggaagg ccgcattact tcgcgacctc agcgatgttg ttcctaacct gaactga       1377
```

```
<210> SEQ ID NO 25
<211> LENGTH: 45
<212> TYPE: DNA
<213> ORGANISM: artificial
<220> FEATURE:
<223> OTHER INFORMATION: Ml-trxBA-fwrd (Primer sequence ml-trxBA-fwrd)
<220> FEATURE:
<221> NAME/KEY: Ml-trxBA-fwrd
<222> LOCATION: (1)..(45)

<400> SEQUENCE: 25
catcaccatc accattccat gaacacaacg cctagtgcgc atgag                        45

<210> SEQ ID NO 26
<211> LENGTH: 48
<212> TYPE: DNA
<213> ORGANISM: artificial
<220> FEATURE:
<223> OTHER INFORMATION: Ml-trxBA-rev (Primer sequence ml-trxBA-rev)
<220> FEATURE:
<221> NAME/KEY: Ml-trxBArev
<222> LOCATION: (1)..(48)

<400> SEQUENCE: 26
ctttgttagc agccggatcc tcagttcagg ttaggaacaa catcgctg                     48

<210> SEQ ID NO 27
<211> LENGTH: 1338
<212> TYPE: DNA
<213> ORGANISM: artificial
<220> FEATURE:
<223> OTHER INFORMATION: histrxB5A (Fusion gene of His-tag and E.coli
      proteins TrxB and TrxA)
<220> FEATURE:
<221> NAME/KEY: histrxB5A
<222> LOCATION: (1)..(1338)

<400> SEQUENCE: 27
atgacacaga gggcccacca tcaccatcac cattccatgg gcacgaccaa acacagtaaa      60
ctgcttatcc tgggttcagg cccggcggga tacaccgctg ctgtctacgc ggcgcgcgcc     120
aacctgcaac ctgtgctgat taccggcatg gaaaaaggcg ccaactgac accaccacg       180 gaagtggaaa actggcctgg cgatccaaac gatctgaccg tccgttatt aatggagcgc      240 atgcacgaac atgccaccaa gtttgaaact gagatcattt ttgatcatat caacaaggtg    300
gatctgcaaa accgtccgtt ccgtctgaat ggcgataacg cgaatacac ttgcgacgcg      360 ctgattattg ccaccggagc ttctgcacgc tatctcggcc tgccctctga agaagccttt     420
aaaggccgtg gggtttctgc ttgtgcaacc tgcgacggtt cttctatcg caaccagaaa      480 gttgcggtca tcggcggcgg caataccgcg gttgaagagg cgctgtatct gtctaacatc     540
gcttcggaag tgcatctgat tcaccgccgt gacggtttcc gcgcggaaaa aatcctcatt     600
aagcgcctga tggataaagt gggagaacggc aacatcattc tgcacaccaa ccgtacgctg    660
gaagaagtga ccggcgatca aatgggtgtc actggcgttc gtctgcgcga tacgcaaaac    720
agcgataaca tcgagtcact cgacgttgcc ggtctgtttg ttgctatcgg tcacagcccg    780
aatactgcga ttttcgaagg gcagctggaa ctggaaaacg ctacatcaa agtacagtcg      840 ggtattcatg gtaatgccac ccagaccagc attcctggcg tctttgccgc aggcgacgtg    900
atggatcaca tttatcgcca ggccattact tcggccggta caggctgcat ggcagcactt     960
gatgcggaac gctacctcga tggtttagct gacgcaggtc cggcccctgg cagcgataaa    1020
```

-continued

```
attattcacc tgactgacga cagttttgac acggatgtac tcaaagcgga cggggcgatc     1080
ctcgtcgatt tctgggcaga gtggtgcggt ccgtgcaaaa tgatcgcccc gattctggat     1140
gaaatcgctg acgaatatca gggcaaactg accgttgcaa aactgaacat cgatcaaaac     1200
cctggcactg cgccgaaata tggcatccgt ggtatcccga ctctgctgct gttcaaaaac     1260
ggtgaagtgg cggcaaccaa agtgggtgca ctgtctaaag gtcagttgaa agagttcctc     1320
gacgctaacc tggcgtaa                                                   1338
```

```
<210> SEQ ID NO 28
<211> LENGTH: 445
<212> TYPE: PRT
<213> ORGANISM: artificial
<220> FEATURE:
<223> OTHER INFORMATION: HisTrxB5A (Fusion protein of His-tag and E.coli
      proteins TrxB and TrxA)
<220> FEATURE:
<221> NAME/KEY: His-TrxB5A
<222> LOCATION: (1)..(445)

<400> SEQUENCE: 28

Met Thr Gln Arg Ala His His His His His His Ser Met Gly Thr Thr
1               5                   10                  15

Lys His Ser Lys Leu Leu Ile Leu Gly Ser Gly Pro Ala Gly Tyr Thr
            20                  25                  30

Ala Ala Val Tyr Ala Ala Arg Ala Asn Leu Gln Pro Val Leu Ile Thr
        35                  40                  45

Gly Met Glu Lys Gly Gly Gln Leu Thr Thr Thr Thr Glu Val Glu Asn
    50                  55                  60

Trp Pro Gly Asp Pro Asn Asp Leu Thr Gly Pro Leu Leu Met Glu Arg
65                  70                  75                  80

Met His Glu His Ala Thr Lys Phe Glu Thr Glu Ile Ile Phe Asp His
                85                  90                  95

Ile Asn Lys Val Asp Leu Gln Asn Arg Pro Phe Arg Leu Asn Gly Asp
            100                 105                 110

Asn Gly Glu Tyr Thr Cys Asp Ala Leu Ile Ile Ala Thr Gly Ala Ser
        115                 120                 125

Ala Arg Tyr Leu Gly Leu Pro Ser Glu Glu Ala Phe Lys Gly Arg Gly
    130                 135                 140

Val Ser Ala Cys Ala Thr Cys Asp Gly Phe Phe Tyr Arg Asn Gln Lys
145                 150                 155                 160

Val Ala Val Ile Gly Gly Gly Asn Thr Ala Val Glu Glu Ala Leu Tyr
                165                 170                 175

Leu Ser Asn Ile Ala Ser Glu Val His Leu Ile His Arg Arg Asp Gly
            180                 185                 190

Phe Arg Ala Glu Lys Ile Leu Ile Lys Arg Leu Met Asp Lys Val Glu
        195                 200                 205

Asn Gly Asn Ile Ile Leu His Thr Asn Arg Thr Leu Glu Glu Val Thr
    210                 215                 220

Gly Asp Gln Met Gly Val Thr Gly Val Arg Leu Arg Asp Thr Gln Asn
225                 230                 235                 240

Ser Asp Asn Ile Glu Ser Leu Asp Val Ala Gly Leu Phe Val Ala Ile
                245                 250                 255

Gly His Ser Pro Asn Thr Ala Ile Phe Glu Gly Gln Leu Glu Leu Glu
            260                 265                 270

Asn Gly Tyr Ile Lys Val Gln Ser Gly Ile His Gly Asn Ala Thr Gln
        275                 280                 285
```

-continued

```
Thr Ser Ile Pro Gly Val Phe Ala Ala Gly Asp Val Met Asp His Ile
    290                 295                 300

Tyr Arg Gln Ala Ile Thr Ser Ala Gly Thr Gly Cys Met Ala Ala Leu
305                 310                 315                 320

Asp Ala Glu Arg Tyr Leu Asp Gly Leu Ala Asp Ala Gly Pro Ala Pro
                325                 330                 335

Gly Ser Asp Lys Ile Ile His Leu Thr Asp Asp Ser Phe Asp Thr Asp
                340                 345                 350

Val Leu Lys Ala Asp Gly Ala Ile Leu Val Asp Phe Trp Ala Glu Trp
                355                 360                 365

Cys Gly Pro Cys Lys Met Ile Ala Pro Ile Leu Asp Glu Ile Ala Asp
    370                 375                 380

Glu Tyr Gln Gly Lys Leu Thr Val Ala Lys Leu Asn Ile Asp Gln Asn
385                 390                 395                 400

Pro Gly Thr Ala Pro Lys Tyr Gly Ile Arg Gly Ile Pro Thr Leu Leu
                405                 410                 415

Leu Phe Lys Asn Gly Glu Val Ala Ala Thr Lys Val Gly Ala Leu Ser
                420                 425                 430

Lys Gly Gln Leu Lys Glu Phe Leu Asp Ala Asn Leu Ala
                435                 440                 445

<210> SEQ ID NO 29
<211> LENGTH: 50
<212> TYPE: DNA
<213> ORGANISM: artificial
<220> FEATURE:
<223> OTHER INFORMATION: vtrxA5-fwrd (Primer vector with trxA for trxB5A
      fusion gene fwrd)
<220> FEATURE:
<221> NAME/KEY: vtrx5A-fwrd
<222> LOCATION: (1)..(50)

<400> SEQUENCE: 29
ctgacgcagg tccggcccct ggcagcgata aaattattca cctgactgac                50

<210> SEQ ID NO 30
<211> LENGTH: 64
<212> TYPE: DNA
<213> ORGANISM: artificial
<220> FEATURE:
<223> OTHER INFORMATION: ftrxB5-rev (Primer insert trxB5 for trxB5A
      fusion gene rev)
<220> FEATURE:
<221> NAME/KEY: ftrxB5-rev
<222> LOCATION: (1)..(64)

<400> SEQUENCE: 30
gtcaggtgaa taattttatc gctgccaggg gccggacctg cgtcagctaa accatcgagg    60
tagc                                                                  64
```